(12) United States Patent
Kearns et al.

(10) Patent No.: US 9,657,108 B2
(45) Date of Patent: May 23, 2017

(54) DOSAGE AND ADMINISTRATION OF ANTI-EGFR THERAPEUTICS

(71) Applicant: Merrimack Pharmaceuticals, Inc., Cambridge, MA (US)

(72) Inventors: Jeffrey David Kearns, Arlington, MA (US); Beni B. Wolf, Lexington, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/867,554

(22) Filed: Sep. 28, 2015

(65) Prior Publication Data

US 2016/0009822 A1 Jan. 14, 2016

Related U.S. Application Data

(63) Continuation of application No. PCT/US2015/030870, filed on May 14, 2015.

(60) Provisional application No. 62/005,401, filed on May 30, 2014, provisional application No. 61/996,819, filed on May 14, 2014.

(51) Int. Cl.

| A61K 39/395 | (2006.01) |
|---|---|
| C07K 16/32 | (2006.01) |
| A61K 45/06 | (2006.01) |
| C07K 16/28 | (2006.01) |
| C07K 16/30 | (2006.01) |
| A61K 9/00 | (2006.01) |
| A61K 31/138 | (2006.01) |
| A61K 31/4745 | (2006.01) |
| A61K 31/573 | (2006.01) |
| C07K 16/40 | (2006.01) |
| A61K 31/135 | (2006.01) |
| A61K 31/167 | (2006.01) |
| A61K 39/00 | (2006.01) |

(52) U.S. Cl.
CPC ............ *C07K 16/32* (2013.01); *A61K 9/0019* (2013.01); *A61K 31/135* (2013.01); *A61K 31/138* (2013.01); *A61K 31/167* (2013.01); *A61K 31/4745* (2013.01); *A61K 31/573* (2013.01); *A61K 39/3955* (2013.01); *A61K 39/39558* (2013.01); *A61K 45/06* (2013.01); *C07K 16/2863* (2013.01); *C07K 16/30* (2013.01); *C07K 16/40* (2013.01); *A61K 2039/505* (2013.01); *A61K 2039/507* (2013.01); *A61K 2039/54* (2013.01); *A61K 2039/545* (2013.01); *C07K 2317/51* (2013.01); *C07K 2317/515* (2013.01); *C07K 2317/56* (2013.01); *C07K 2317/565* (2013.01); *C07K 2317/732* (2013.01); *C07K 2317/734* (2013.01); *C07K 2317/76* (2013.01)

(58) Field of Classification Search
None
See application file for complete search history.

(56) References Cited

U.S. PATENT DOCUMENTS

| 7,226,592 | B2 | 6/2007 | Kreysch |
|---|---|---|---|
| 7,498,142 | B2 | 3/2009 | Yarden et al. |
| 7,771,958 | B2 | 8/2010 | Bacus et al. |
| 7,887,805 | B2 | 2/2011 | Pedersen et al. |
| 8,008,003 | B2 | 8/2011 | Baker et al. |
| 8,147,867 | B2 | 4/2012 | Hong et al. |
| 8,329,213 | B2 | 12/2012 | Hong et al. |
| 8,414,896 | B2 | 4/2013 | Pedersen et al. |
| 8,691,231 | B2 | 4/2014 | Bukhalid et al. |
| 8,703,181 | B2 | 4/2014 | Hong et al. |
| 8,830,814 | B2 | 9/2014 | Manakkal et al. |
| 8,992,970 | B2 | 3/2015 | Hong et al. |
| 9,044,460 | B2 | 6/2015 | Bukhalid et al. |
| 9,226,964 | B2 | 1/2016 | Bukhalid et al. |
| 9,339,497 | B2 | 5/2016 | Bayever et al. |
| 2004/0052785 | A1 | 3/2004 | Goodman et al. |
| 2005/0003403 | A1 | 1/2005 | Rossi et al. |
| 2006/0228355 | A1 | 10/2006 | Laeremans et al. |
| 2008/0206236 | A1 | 8/2008 | Haurum |
| 2008/0299120 | A1 | 12/2008 | Miller et al. |
| 2009/0004192 | A1 | 1/2009 | Pedersen et al. |
| 2009/0155288 | A1 | 6/2009 | Yarden et al. |
| 2009/0181855 | A1 | 7/2009 | Vasquez et al. |
| 2009/0226447 | A1 | 9/2009 | Boone et al. |
| 2009/0298701 | A1 | 12/2009 | Baker et al. |
| 2010/0056383 | A1 | 3/2010 | Ririe et al. |
| 2011/0287002 | A1 | 11/2011 | Bukhalid et al. |

(Continued)

FOREIGN PATENT DOCUMENTS

| EP | 2554551 A1 | 2/2013 |
|---|---|---|
| WO | 02/055106 A2 | 7/2002 |

(Continued)

OTHER PUBLICATIONS

Ko, A.H., et al., "A multinational phase 2 study of nanoliposomal irinotecan sucrosofate (PEP02, MM-398) for patients with gemcitabine-refractory metastatic pancreatic cancer," British Journal of Cancer, vol. 109: 920-925, doi: 10.1038/bjc.2013.408 (2013).
U.S. Appl. No. 13/100,920, filed May 4, 2011, Raghida Bukhalid.
U.S. Appl. No. 14/724,058, filed May 28, 2015, Raghida Bukhalid.
U.S. Appl. No. 14/847,351, filed Sep. 8, 2015, Raghida Bukhalid.
U.S. Appl. No. 13/488,270, filed Jun. 4, 2012, Raghida Bukhalid.
U.S. Appl. No. 14/181,307, filed Feb. 14, 2014, Raghida Bukhalid.
U.S. Appl. No. 14/833,834, filed Aug. 24, 2015, Raghida Bukhalid.
U.S. Appl. No. 14/147,331, filed Jan. 3, 2015, Raghida Bukhalid.
U.S. Appl. No. 14/266,387, filed Apr. 30, 2014, Raghida Bukhalid.
U.S. Appl. No. 14/847,291, filed Sep. 8, 2015, Raghida Bukhalid.

(Continued)

*Primary Examiner* — Michael Pak
(74) *Attorney, Agent, or Firm* — Nelson Mullins Riley & Scarborough LLP; Jane E. Remillard, Esq.; Jill Gorny Sloper, Esq.

(57) ABSTRACT

Methods for optimizing a therapeutic response in a patient (e.g., a cancer patient) to an anti-EGFR therapy, and methods for preventing or ameliorating infusion reactions in a patient receiving an anti-EGFR therapy are disclosed.

6 Claims, 8 Drawing Sheets

(56) References Cited

U.S. PATENT DOCUMENTS

| | | |
|---|---|---|
| 2012/0308576 A1 | 12/2012 | Bukhalid et al. |
| 2014/0127207 A1 | 5/2014 | Bukhalid et al. |
| 2014/0170668 A1 | 6/2014 | Bukhalid et al. |
| 2014/0234314 A1 | 8/2014 | Bukhalid et al. |
| 2015/0231238 A1 | 8/2015 | Garcia et al. |
| 2015/0368346 A1 | 12/2015 | Bukhalid et al. |
| 2015/0368347 A1 | 12/2015 | Bukhalid et al. |
| 2015/0368361 A1 | 12/2015 | Bukhalid et al. |
| 2015/0376284 A1 | 12/2015 | Bukhalid et al. |
| 2016/0002339 A1 | 1/2016 | Bukhalid et al. |
| 2016/0009822 A1 | 1/2016 | Kearns et al. |
| 2016/0083800 A1 | 3/2016 | Bukhalid et al. |
| 2016/0251445 A1 | 9/2016 | Kearns et al. |

FOREIGN PATENT DOCUMENTS

| | | |
|---|---|---|
| WO | 2004/032961 A1 | 4/2004 |
| WO | 2004/094613 A2 | 11/2004 |
| WO | 2008/095504 A1 | 8/2008 |
| WO | 2008/104183 A2 | 9/2008 |
| WO | 2009/030239 A1 | 3/2009 |
| WO | 2010/019952 A2 | 2/2010 |
| WO | 2011/0132182 A1 | 10/2011 |
| WO | 2011/140151 A1 | 11/2011 |
| WO | 2011/140254 A1 | 11/2011 |
| WO | 2013/006547 A2 | 1/2013 |
| WO | 2013/138371 A1 | 9/2013 |
| WO | 2013/188586 A1 | 12/2013 |

OTHER PUBLICATIONS

U.S. Appl. No. 14/847,297, filed Sep. 8, 2015, Raghida Bukhalid.
U.S. Appl. No. 14/847,304, filed Sep. 8, 2015, Raghida Bukhalid.
U.S. Appl. No. 13/100,920, Jan. 27, 2015.
U.S. Appl. No. 13/100,920, Jan. 7, 2014.
U.S. Appl. No. 13/100,920, Aug. 28, 2013.
U.S. Appl. No. 13/488,270, Nov. 15, 2013.
U.S. Appl. No. 13/488,270, Jul. 8, 2013.
U.S. Appl. No. 13/488,270, Jan. 16, 2013.
U.S. Appl. No. 13/488,270, Oct. 23, 2012.
U.S. Appl. No. 14/147,331, Sep. 29, 2015.
U.S. Appl. No. 14/147,331, Jun. 18, 2015.
U.S. Appl. No. 14/147,331, Dec. 22, 2014.
U.S. Appl. No. 14/181,307, Jul. 20, 2015.
U.S. Appl. No. 14/181,307, Apr. 20, 2015.
U.S. Appl. No. 14/181,307, Dec. 18, 2014.
U.S. Appl. No. 14/266,387, Jul. 20, 2015.
International Preliminary Report on Patentability and Written Opinion for Application No. PCT/US2012/045235, 7 pages, dated Jan. 7, 2014.
International Preliminary Report on Patentability for Application No. PCT/US2011/035238, 7 pages, dated Nov. 6, 2012.
International Search Report and Written Opinion, PCT/US2015/030870, dated Oct. 12, 2015, 19 pages.
International Search Report for Application No. PCT/US2012/045235, 5 pages, dated Feb. 20, 2013.
Invitation to Pay Additional Fees, and, Where Applicable, Protest Fees, PCT/US2015/030870, dated Aug. 5, 2015, 9 pages.
Kamat, Vishal et al., "Enhanced EGFR inhibition and distinct epitope recognition by EGFR antagonistic mAbs C225 and 425," Cancer Biology & Therapy, vol. 7(5):726-733 (2008).
Modjtahedi, H. et al., "Antitumor Activity of Combinations of Antibodies Directed Against Different Epitopes on the Extracellular Domain of the Human EGF Receptor," Cell Biophysics, vol. 22(1-3):129-146 (1993).
Nahta, Rita et al., "The HER-2-Targeting Antibodies Trastuzumab and Pertuzumab Synergistically Inhibit the Survival of Breast Cancer Cells," Cancer Research, vol. 64:2343-2346 (2004).
Nielsen, Dorte L. et al., "Re-treatment with cetuximab in patients with severe hypersensitivity reactions to cetuximab. Two case reports," ACTA Oncologica, vol. 45 (8,1), pp. 1137-1138 (Jan. 1, 2006).
Nowakowski, A. et al., "Potent neutralization of botulinum neurotoxin by recombinant oligoclonal antibody," PNAS, vol. 99(17):11346-11350 (2002).
Paz-Ares, L. G. et al., "Phase I Pharmacokinetic and Pharmacodynamic Dose-Escalation Study of RG7160 (GA201), the First Glycoengineered Monoclonal Antibody Against the Epidermal Growth Factor Receptor, in Patients With Advanced Solid Tumors," Journal of Clinical Oncology, vol. 29 (28), pp. 3783-3790 (Oct. 2011).
Pedersen, Mikkel Wandahl et al., "Sym004: A Novel Synergistic Anti-Epidermal Growth Factor Receptor Antibody Mixture with Superior Anticancer Efficacy," Cancer Research, vol. 70(2):588-597 (2010).
Perera, Rushika M. et al., "Treatment of Human Tumor Xenografts with Monoclonal Antibody 806 in Combination with a Prototypical Epidermal Growth Factor Receptor-Specific Antibody Generates Enhanced Antitumor Activity," Clinical Cancer Research, vol. 11(17):6390-6399 (2005).
Regales, Lucia et al., "Dual targeting of EGFR can overcome a major drug resistance mutation in mouse models of EGFR mutant lung cancer," The Journal of Clinical Investigation, vol. 119(10):3000-3010 (2009).
Saridaki, Zacharenia et al., "Impact of KRAS, BRAF, PIK3CA Mutations, PTEN, AREG, EREG Expression and Skin Rash in 2nd Line Cetuximab-Based Therapy of Colotectal Cancer Patients," PLoS One, vol. 6(1):e15980, 1-13 (2011).
Schoeberl, Birgit et al., "Therapeutically Targeting ErbB3: A Key Node in Ligand-Induced Activation of the ErbB Receptor-PI3K Axis," Science Signaling, vol. 2(77):ra31, 1-14 (2009).
Siena, Salvatore et al., "Biomarkers Predicting Clinical Outcome of Epidermal Growth Factor Receptor-Targeted Therapy in Metastatic Colorectal Cancer," J. Natl. Cancer, vol. 101:1-17 (2009).
Skartved, Niels Jorgen Ostergaard et al., "Preclinical Pharmacokinetics and Safety of Sym004: A Synergistic Antibody Mixture Directed against Epidermal Growth Factor Receptor," Clinical Cancer Research, vol. 17 (18):5962-5972 (2011).
Spangler, Jamie B. et al., "Combination antibody treatment down-regulates epidermal growth factor receptor by inhibiting endosomal recycling," PNAS, vol. 107(30):13252-13257 (2010).
Spiridon, Camelia I. et al., "Targeting Multiple Her-2 Epitopes with Monoclonal Antibodies Results in Improved Antigrowth Activity of a Human Breast Cancer Cell Line In Vitro and In Vivo," Clinical Cancer Research, vol. 8:1720-1730 (2002).
Tabernero, Josep et al., "Pharmacogenomic and Pharmacoproteomic Studies of Cetuximab in Metastatic Colorectal Cancer: Biomarker Analysis of a Phase I Dose-Escalation Study," J. Clin. Oncol., vol. 28:1181-1189(2010).
Tebbutt, N. et al., "Targeting the ERBB Family in Cancer: couples Therapy," Nature Cancer Reviews, vol. 13, pp. 633-673 (2013).
Tomax, T., "Immunology," Laboratory of Immunology, National Institute of Allergy and Infectious Diseases, National Institutes of Health, Edited by Paul W., Mir, Moscow "World", vol. 3 (1989), pp. 1-6.
Wikipedia, "Competitive inhibition," retrieved online at: http://en.wikipedia.org/w/index.php?title=Competitive_inhibition, 5 pages (2011).
Yonesaka, Kimio et al., "Autocrine Production of Amphiregulin Predicts Sensitivity to Both Gefitinib and Cetuximab and EGFR Wild-type Cancers," Ciin. Cancer Res., vol. 14(21):6963-6973 (2008).
Baker, J.B. et al., "Tumour gene expression predicts response to cetuximab in patients with KRAS wild-type metastatic colorectal cancer," British Journal of Cancer, vol. 104:488-495, (2011 ).
International Search Report and Written Opinion for Application No. PCT/US2011/035238, 10 pages, dated Oct. 17, 2011.
ClinicalTrials.gov, "A Phase I Study of Cetuxinnab in Combination With Gefitinib in Patients With Advanced/Metastatic Non-Small Cell Lung Cancer," Study NCT00162318, Bristol-Myers Squibb, 3 pages, date received Sep. 9, 2005.
ClinicalTrials.gov, "A Study of BIBW 2992 (Afatinib) in Patients With Metastatic Colorectal Cancer," Study NCT01152437, Boehringer Ingelheim Pharmaceuticals, 4 pages, date received Jun. 28, 2010.

(56) References Cited

OTHER PUBLICATIONS

ClinicalTrials.gov, "A Study of R1507 in Combination With Multiple Standard Chemotherapy Treatments in Patients With Advanced Solid Tumors," Study NCT00811993, Hoffmann-La Roche, 6 pages, dated received Dec. 18, 2008.
ClinicalTrials.gov, "A Study of SCH 717454 in Combination With Different Treatment Regimens in Subjects With Advanced Solid Tumors (P04722)," Study NCT00954512, Schering-Plough, 5 pages, dated received Jul. 23, 2009.
ClinicalTrials.gov, "An Umbrella, Modular Study Based on Epidermal Growth Factor Receptors (EGFR) Mutation Status," Study NCT00903734, M.D. Anderson Cancer Center, 5 pages, dated received May 14, 2009.
ClinicalTrials.gov, "Bevacizumab and Gemcitabine Combined With Either Cetuximab or Erlotinib in Treating Patients With Advanced Pancreatic Cancer," Study NCT00091026, National Cancer Institute (NCI), 6 pages, dated received Sep. 7, 2004.
ClinicalTrials.gov, "Bevacizumab in Multiple Phase I Combinations," Study NCT00543504, M.D. Anderson Cancer Center, 7 pages, dated received Oct. 11, 2007.
ClinicalTrials.gov, "BIBW 2992 (Afatinib) in Head & Neck Cancer," Study NCT00514943, Boehringer Ingelheim Pharmaceuticals, 5 pages, dated received Aug. 9, 2007.
ClinicalTrials.gov, "Carboplatin, Paclitaxel, Cetuximab, and Erlotinib Hydrochloride in Treating Patients With Metastatic or Recurrent Head and Neck Squamous Cell Cancer," Study NCT01316757, Fox Chase Cancer Center, 7 pages, dated received Mar. 8, 2011.
ClinicalTrials.gov, "Cetuximab in Patients With Lung Adenocarcinoma Receiving Erlotinib That Have Developed 'Acquired Resistance' to Erlotinib," Study NCT00716456, Memorial Sloan-Kettering Cancer Center, 1 page, dated received Jul. 15, 2008.
ClinicalTrials.gov, "Clinical and Pathologic Studies of Patients Undergoing Treatment With EGFR Inhibitors," Study NCT01137162, Stanford University, 1 page, dated received Jun. 1, 2010.
ClinicalTrials.gov, "Combination Study of BMS-754807 and Erbitux in Subjects With Advanced or Metastatic Solid Tumors," Study NCT00908024, Bristol-Myers Squibb, 4 pages, dated received May 22, 2009.
ClinicalTrials.gov, "Dual Epidermal Growth Factor Receptor Inhibition With Erlotinib and Panitumumab With or Without Chemotherapy for Advanced Colorectal Cancer," Study NCT00940316, Northwestern University, 1 page, dated received Jul. 15, 2011.
ClinicalTrials.gov, "Dual Inhibition of EGFR Signalling Using the Combination of Cetuximab and Erlotinib (Dux)," Study NCT00784667, Austin Health, 1 page, dated received Nov. 3, 2008.
ClinicalTrials.gov, "Erlotinib and Cetuximab in Treating Patients With Advanced Gastrointestinal Cancer, Head and Neck Cancer, Non-Small Cell Lung Cancer, or Colorectal Cancer," Study NCT00397384, Vanderbilt-Ingram Cancer Center, 1 page, dated received Nov. 8, 2006.
ClinicalTrials.gov, "Erlotinib and Cetuximab in Treating Patients With Advanced Solid Tumors With Emphasis on Non-Small Cell Lung Cancer," Study NCT00408499, University of California, Davis, 1 page, dated received Dec. 6, 2006.
ClinicalTrials.gov, "Erlotinib and Cetuximab With or Without Bevacizumab in Treating Patients With Metastatic or Unresectable Kidney, Colorectal, Head and Neck, Pancreatic, or Non-Small Cell Lung Cancer," Study NCT00101348, National Cancer Institute (NCI), 6 pages, dated received Jan. 7, 2005.
ClinicalTrials.gov, "Erlotinib and Gemcitabine With or Without Panitumumab in Treating Patients With Metastatic Pancreatic Cancer," Study NCT00550836, National Cancer Institute (NCI), 6 pages, dated received Oct. 26, 2007.
ClinicalTrials.gov, "Erlotinib in Combination With Cetuximab," Study NCT00895362, M.D. Anderson Cancer Center, 5 pages, dated received May 6, 2009.
ClinicalTrials.gov, "Evaluating Preventive Therapy With Oint Threolone, Synthomycine or Aqua Cream Lotion, for EGFR'I Induced Acneiform Rash," Study NCT01256437, Rabin Medical Center, 4 pages, dated received Dec. 7, 2010.
ClinicalTrials.gov, "Histological Characterization and Differentiation of Rash From Other Epidermal Growth Factor Receptor (EGFR) Inhibitors," Study NCT00709878, Northwestern University, 1 page, dated received Jul. 1, 2008.
ClinicalTrials.gov, "Individualized Drug Treatment Selection Process for Treating Patients with Pancreatic Cancer That Can Be Removed by Surgery," Study NCT00276744, Sidney Kimmel Comprehensive Cancer Center, 5 pages, dated received Jan. 12, 2006.
ClinicalTrials.gov, "Lapatinib and Cetuximab in Patients With Solid Tumors (TYKERB-ITUX 1)," Study NCT01184482, Georgetown University, 4 pages, dated received Aug. 17, 2010.
ClinicalTrials.gov, "Menadione Topical Lotion in Treating Skin Discomfort and Psychological Distress in Patients With Cancer Receiving Panitumumab, Erlotinib Hydrochloride, or Cetuximab," Study NCT01393821, Mayo Clinic, 5 pages, dated received Jun. 27, 2011.
ClinicalTrials.gov, "Pharmacodynamic Separation of Pemetrexed and Erlotinib as Second-line Therapy in Patients With Advanced Non-small Cell Lung Cancer (NSCLC)," Study NCT00950365, Montefiore Medical Center, 1 page, dated received Jul. 30, 2009.
ClinicalTrials.gov, "Pharmocokinetic/Pharmacodynamic (PK/PD) Study of the Combination Cetuximab/Gefitinib," Study NCT00820417, Harrison Clinical Research, 1 page, dated received Jan. 9, 2009.
ClinicalTrials.gov, "Phase 1 Trial With SIR-Spheres and Cetuximab +/− Erlotinib," Study NCT01432119, M.D. Anderson Cancer Center, 6 pages, dated received Sep. 8, 2011.
ClinicalTrials.gov, "Safety and Efficacy of Radiation/Cetuximab Plus EGFR Antisense DNA for Head and Neck Squamous Cell Carcinoma," Study NCT00903461, University of Pittsburgh, 5 pages, dated received May 14, 2009.
ClinicalTrials.gov, "Study About Preventive Treatment of Folliculitis Induced by Epidermal Growth Factor Receptor (EGF-R) Inhibitors (DIPROCOL)," Study NCT00910676, Centre Oscar Lambret, 4 pages, dated received May 29, 2009.
ClinicalTrials.gov, "Study of AMG 479 With Biologics or Chemotherapy for Subjects With Advanced Solid Tumors," Study NCT00974896, Amgen, 5 pages, dated received Sep. 10, 2009.
ClinicalTrials.gov, "Study of Cetuximab in Combination With Tarceva in Patients With Solid Tumors," Study NCT00207077, Bristol-Myers Squibb, 3 pages, dated received Sep. 12, 2005.
ClinicalTrials.gov, "Sym004 in Patients With Advanced Solid Tumors," Study NCT01117428, Symphogen A/S, 1 pages, dated received Apr. 23, 2010.
ClinicalTrials.gov, "Sym004 in SCCHN Patients Failing Anti-EGFR Based Therapy," Study NCT01417936, Symphogen A/S, 1 page, dated received Jul. 15, 2011.
ClinicalTrials.gov, "Temsirolimus (Torisel) and Erlotinib (Tarceva) in Platinum-Refractory/Ineligible, Advanced, Squamous Cell Carcinoma," Study NCT01009203, New Mexico Cancer Care Alliance, 4 pages, dated received Nov. 5, 2009.
ClinicalTrials.gov, "Tetracycline in Preventing Skin Rash in Patients Who Are Receiving Drugs Such as Gefitinib and Cetuximab for Cancer," Study NCT00091247, National Cancer Institute (NCI), 1 page, dated received Sep. 7, 2004.
ClinicalTrials.gov, "Topical Sunscreen in Preventing Skin Rash in Patients Receiving Drugs Such as Erlotinib or Cetuximab for Cancer," Study NCT00362986, National Cancer Institute (NCI), 4 pages, dated received Aug. 10, 2006.
ClinicalTrials.gov, "Trial of BIBW 2992 (Afatinib) + Cetuximab in Non-Small Cell Lung Cancer," Study NCT01090011, Boehringer Ingelheim Pharmaceuticals, 1 page, dated received Mar. 10, 2010.
ClinicalTrials.gov, "Validation of Cancer Questionnaire for Skin Toxicities in Patients With Colorectal Cancer or Lung Cancer Receiving Cetuximab, Panitumumab, or Erlotinib Hydrochloride," Study NCT01416688, National Cancer Institute (NCI), 5 pages, dated received Aug. 12, 2011.

(56) References Cited

OTHER PUBLICATIONS

ClinicalTrials.gov, "ZD6474, Cetuximab, and Irinotecan in Patients With Metastatic Colorectal Cancer," Study NCT00436072, Dana-Farber Cancer Institute, 5 pages, dated received Feb. 15, 2007.
Cochran, Jennifer R. et al., "Domain-level antibody epitope mapping through yeast surface display of epidermal growth factor receptor fragments," Journal of Immunological Methods, vol. 287:147-158 (2004).
Dienstmann, R. et al., "Phase I trial of the first-in-class EGFR antibody mixture, Sym004, in patients with advanced solid tumors. ", Journal of Clinical Oncology, vol. 29, No. supl. 1, Abstract 3089, 2 pages (Jan. 2011).
European Search Report for Application No. 12275088.8, 12 pages, dated Oct. 11, 2012.
Fogler, William E. et al., "Enhanced Cytotoxicity against Colon Carcinoma by Combinations of Noncompeting Monoclonal Antibodies to the 17-1A Antigen," Cancer Research, vol. 48:6303-6308 (1998).
Friedman, Lilach M. et al., "Synergistic down-regulation of receptor tyrosine kinases by combinations of mAbs: Implications for cancer innumotherapy," PNAS, vol. 102(6):1915-1920 (2005).
Grandis, Jennifer Rubin et al., "Levels of TGF-alpha and EGFR Protein in Head and Neck Squamous Cell Carcinoma and Patient Survival," Journal of the National Cancer Institute, vol. 90(11):824-832 (1998).
Arena, S. et al., "Emergence of Multiple EGFR Extracellular; Mutations during Cetuximab Treatment in Colorectal cancer," Clin Cancer Res., 21(9): 2157-2166 (2015).
Arena, S. et al., "MM-151 overcomes acquired resistance to cetuximab and panitumumab in colorectal cancer cells harboring EGFR extracellular domain mutations," ACR-NCI-EORTC International Conference on Molecular Targets and Cancer Therapies, Abstract No. LB-B05, 1 page (2015).
Buch, I. et al., "Computational Modeling of an Epidermal Growth Factor Receptor Single-Mutation Resistance to etuximab in Colorectal Cancer Treatment," Journal of Chemical Information and Modeling, vol. 53: 3123-3126 (2013).
Dienstmann, R. et al., "Safety and Activity of the First-in-Class Sym004 Anti-EGFR Antibody Mixture in Patients with Refractory Colorectal Cancer," Cancer Discovery, AACR, 5(6): 598-609 (2015).
Esposito, C. et al., "The 5492R EGFR ectodomain mutation is never detected in KRAS wild-type colorectal carcinoma before exposure to EGFR monoclonal antibodies," Cancer Biology & Therapy, vol. 14(12) : 1143-1146 (2013).
Iida, M. et al., "Sym004, a Novel EGFR Antibody Mixture, Can Overcome Acquired Resistance to Cetuximab," vol. 15 (10): 1196-1206 (2013).
Kearns, J. et al., "Enhanced Targeting of the EGFR Network with MM-151, an Oligoclonal Anti-EGFR Antibody Therapeutic," Molecular Cancer Therapeutics, American Association for Cancer Research, 13 pages (2015).
Montagut, C. et al., "Identification of a mutation in the extracellular domain of the Epidermal Growth Factor Receptor conferring cetuximab resistance in colorectal cancer," Nature Medicine, vol. 18(2):221-223 (2012).
Morelli, M. et al. "Characterizing the patterns of clonal selection in circulating tumor DNA from patients with colorectal Cancer refractory to anti-EGFR treatment," Annals of Oncology, vol. 26: 731-736 (2015).
Morelli, M. et al., "Frequency of concurrent gene mutations and copy number alterations in circulating cell-free DNA (cfDNA) from refractory metastatic CRC patients," American Society of Clinical Oncology, Tumour Biology, General Joster Session (Board #399), Sat. 1:15 PM-5:00 PM (Abstract 11117) 1 page (2014).
Morelli, M. et al., "High frequency of concurrent gene mutations and copy number alterations in circulating cell-free DNA (cfDNA) from refractory metastatic CRC patients," The University of Texas, MD Anderson Cancer Center, Poster presentation, Poster ID # 11117 ASCO, 1 page (2014).
Newhall, K. et al., "Frequency of S492R Mutations in the Epidermal Growth Factor Receptor: Analysis of Plasma DNA from Metastic Colorectal Cancer Patients Treated with Panitumumab or Cetuximab Monotherapy," Annals of Oncology, Oral Abstracts (Abstract # (0/0011), vol. 25(2):1 page (2014).
ONIVYDE US prescribing information, approved Oct. 22, 2015, 18 pages.
Tougeron, D. et al., "Epidermal growth factor receptor (EGFR) and KRAS mutations during chemotherapy plus anti-EGFR monoclonal antibody treatment in metastatic colorectal cancer," Cancer Chemotherapy Pharmacol., vol. 72: 397-403 (2013).
Voigt, M. et al. "Functional Dissection of the Epidermal Growth Factor Receptor Epitopes Targeted by Panitumumab and Cetuximab," Neoplasua, vol. 14: 1023-1031 (2012).
U.S. Appl. No. 14/724,058, filed May 28, 2015, R. Bukhalid, Jun. 15, 2016.
Arena, S. et al, "MM-151 overcomes acquired resistance to cetuximab and panitumumab in colorectal cancers harboring EGFR extracellular domain mutations," Science Translational Medicine, (www.ScienceTranslationalMedicine.org), vol. 8 (Issue 324): 1-11 (2016) Retrieved Feb. 3, 2016.
Beeram, M. et al., "A first-in-human study evaluating safety and pharmacology of MM-151, a novel oligoclonal anti-EGFR antibody combination in patients with refractory solid tumors," The European Organization for Research and Treatment of Cancer (EORTC), Nov. 20, 2014, Abstract No. 329, Poster Presentation, 1 page.
Braig, F. et al., "Epidermal growth factor receptor mutation mediates cross-resistance to panitumumab and aetuximab in gastrointestinal cancer," Oncotarget, vol. 6(14)12035-12047 (2015).
Bukhalid, R. et al., "Therapeutically Targeting EGFR activation by high-affinity ligands with MM-151, a super-potent mixture of three human antibody antagonists," World Conference on Lung Cancer, Jul. 3-7, 2011, Abstract P2.070, Joster Presentation, 1 page.
European Search Report, EP Application No. 16173573.3, dated Jul. 27, 2016, 5 pages.
Gerami-Moayed, N. et al., "Preclinical Characterization of MM-151, an Oligoclonal Antibody Therapeutic That Targets EGFR by Three Distinct Mechanisms of Action," The European Organization for Research and Treatment of Cancer (EORTC) , EORTC/AACR/NCI Conference 2014 in Barcelona, Nov. 19, 2014, Abstract No. 152, Poster presentation, 1 page.
Harb, W. et al. "A First-in-Human Study Evaluating Safety and Pharmacology of MM-151, a Novel Oligoclonal anti-EGFR antibody combination in patients with refractory solid tumors," European Society for Medical Oncology, Sep. 26-30, 2014, Poster Presentation, 1 page.
Hatakeyama, H. et al., "Regulation of Heparin-Binding EGF-Like Growth Factor by MiR-212 and Acquired Cetuximab-Resistance in Head and Neck Squamous Cell Carcinoma," PLoS One, vol. 5(9):e12702, 1-13 (2010).
International Search Report and Written Opinion, PCT/2016/028987, Jul. 20, 2016, 15 pages.
Lieu, C. et al., "Phase 1 Trial of MM-151, a novel oligoclonal anti-EGFR antibody combination in patients with refractory solid tumors," American Society of Clinical Oncology, May 30, 2014-Jun. 3,2014, Poster Presentation, 1 page.
Lieu, C. et al., "Safety, pharmacology, and preliminary activity of MM-151: an oligoclonal anti-EGFR Therapeutic in patients with cetuximab-resistant CRC and other refractory solid tumors," American Society of Clinical Oncology, Jan. 15-17, 2015, Abstract No. 647, Poster Presentation, 1 page.
Price, T. et al., "Prevalence and Outcomes of Patients with EGFR S492R Ectodomain Mutation in ASPECCT: Panitumumab vs. Cetuximab in Patients with Chemorefractory Wild-type KRAS Exon 2 Metastatic Colorectal Cancer," ASCO, GI, Poster Presentation (Abstract 740) 1 page, Jan. 15-17, 2015.
Tan, G. et al., "Mechanism of action of MM-151, a mixture of three human antibody antagonists targeting EGFR," American Association for Cancer Research (AACR), Nov. 12-16, 2011, Abstract A210, Poster Presentation, 1 page.
Wainszelbaum, M. et al., "Inhibition of ERBB3 with MM-121, IGF-1R with MM-141 or Met with MM-131 increases the activity of EGFR inhibitor MM-151 in colorectal cancer models expressing

(56) References Cited

OTHER PUBLICATIONS multiple resistance ligands," ACR-NCI-EORTC International Conference on Molecular Targets and Cancer Therapies, Abstract No. LB-C25,1 page, Nov. 5-9, 2015.
Werner, S. et al., "Therapeutically Targeting High-Affinity Ligand Activation of EGFR with MM-151, an oligoclonal therapeutic," American Association for Cancer Research (AACR), Nov. 12-16, 2011, Abstract P.A144, Poster Presentation, 1 page.
U.S. Appl. No. 15/234,402, filed Aug. 11, 2016, Raghida Bukhalid.
U.S. Appl. No. 15/137,081, filed Apr. 25, 2016, Sabrina Arena.
U.S. Appl. No. 15/156,752, filed May 17, 2016, Jeffrey David Kearns.

SEQUENCE LISTING

```
<160> NUMBER OF SEQ ID NOS: 24

<210> SEQ ID NO 1
<211> LENGTH: 140
<212> TYPE: PRT
<213> ORGANISM: Homo sapiens

<400> SEQUENCE: 1

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Ser Ile Ile Pro Ile Phe Gly Thr Val Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Pro Ser Val Asn Leu Tyr Trp Tyr Phe Asp
        115                 120                 125

Leu Trp Gly Arg Gly Thr Leu Val Thr Val Ser Ser
    130                 135                 140

<210> SEQ ID NO 2
<211> LENGTH: 127
<212> TYPE: PRT
<213> ORGANISM: Homo sapiens

<400> SEQUENCE: 2
```

Met Gly Thr Pro Ala Gln Leu Leu Phe Leu Leu Leu Trp Leu Pro
1               5                   10                  15

Asp Thr Thr Gly Asp Ile Gln Met Thr Gln Ser Pro Ser Thr Leu Ser
            20                  25                  30

Ala Ser Val Gly Asp Arg Val Thr Ile Thr Cys Arg Ala Ser Gln Ser
        35                  40                  45

Ile Ser Ser Trp Trp Ala Trp Tyr Gln Gln Lys Pro Gly Lys Ala Pro
50                  55                  60

Lys Leu Leu Ile Tyr Asp Ala Ser Ser Leu Glu Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln Gln Tyr His
            100                 105                 110

Ala His Pro Thr Thr Phe Gly Gly Gly Thr Lys Val Glu Ile Lys
        115                 120                 125

<210> SEQ ID NO 3
<211> LENGTH: 138
<212> TYPE: PRT
<213> ORGANISM: Homo sapiens

<400> SEQUENCE: 3

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Gly Ser Tyr Ala Ile Ser Trp Val Arg Gln Ala Pro Gly Gln Gly Leu
50                  55                  60

Glu Trp Met Gly Ser Ile Ile Pro Ile Phe Gly Ala Ala Asn Pro Ala
65                  70                  75                  80

Gln Lys Ser Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Lys Met Gly Arg Gly Lys Val Ala Phe Asp Ile Trp
        115                 120                 125

Gly Gln Gly Thr Met Val Thr Val Ser Ser
        130                 135

<210> SEQ ID NO 4
<211> LENGTH: 133
<212> TYPE: PRT
<213> ORGANISM: Homo sapiens

<400> SEQUENCE: 4

Met Gly Thr Pro Ala Gln Leu Leu Phe Leu Leu Leu Trp Leu Pro
1               5                   10                  15

Asp Thr Thr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Tyr Ser Pro Asn Asn Lys Asn Tyr Leu Ala Trp Tyr Gln Gln
50                  55                  60

```
Lys Pro Gly Gln Pro Pro Lys Leu Leu Ile Tyr Trp Ala Ser Thr Arg
 65                  70                  75                  80

Glu Ser Gly Val Pro Asp Arg Phe Ser Gly Ser Gly Ser Gly Thr Asp
                 85                  90                  95

Phe Thr Leu Thr Ile Ser Ser Leu Gln Ala Glu Asp Val Ala Val Tyr
            100                 105                 110

Tyr Cys Gln Gln Tyr Tyr Gly Ser Pro Ile Thr Phe Gly Gly Gly Thr
        115                 120                 125

Lys Val Glu Ile Lys
130

<210> SEQ ID NO 5
<211> LENGTH: 142
<212> TYPE: PRT
<213> ORGANISM: Homo sapiens

<400> SEQUENCE: 5

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Ala Phe
        35                  40                  45

Thr Ser Tyr Gly Ile Asn Trp Val Arg Gln Ala Pro Gly Gln Gly Leu
    50                  55                  60

Glu Trp Met Gly Trp Ile Ser Ala Tyr Asn Gly Asn Thr Tyr Tyr Ala
65                  70                  75                  80

Gln Lys Leu Arg Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Leu Gly Gly Tyr Gly Ser Gly Ser Val Pro
        115                 120                 125

Phe Asp Pro Trp Gly Gln Gly Thr Leu Val Thr Val Ser Ser
    130                 135                 140

<210> SEQ ID NO 6
<211> LENGTH: 128
<212> TYPE: PRT
<213> ORGANISM: Homo sapiens

<400> SEQUENCE: 6

Met Gly Thr Pro Ala Gln Leu Leu Phe Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Asp Tyr Arg
            100                 105                 110
```

Thr Trp Pro Arg Arg Val Phe Gly Gly Gly Thr Lys Val Glu Ile Lys
        115                 120                 125

<210> SEQ ID NO 7
<211> LENGTH: 5
<212> TYPE: PRT
<213> ORGANISM: Homo sapiens

<400> SEQUENCE: 7

Ser Tyr Ala Ile Ser
1               5

<210> SEQ ID NO 8
<211> LENGTH: 10
<212> TYPE: PRT
<213> ORGANISM: Homo sapiens

<400> SEQUENCE: 8

Ile Ile Pro Ile Phe Gly Thr Val Asn Tyr
1               5                   10

<210> SEQ ID NO 9
<211> LENGTH: 6
<212> TYPE: PRT
<213> ORGANISM: Homo sapiens

<400> SEQUENCE: 9

Asp Pro Ser Val Asn Leu
1               5

<210> SEQ ID NO 10
<211> LENGTH: 8
<212> TYPE: PRT
<213> ORGANISM: Homo sapiens

<400> SEQUENCE: 10

Gln Ser Ile Ser Ser Trp Trp Ala
1               5

<210> SEQ ID NO 11
<211> LENGTH: 5
<212> TYPE: PRT
<213> ORGANISM: Homo sapiens

<400> SEQUENCE: 11

Asp Ala Ser Ser Leu
1               5

<210> SEQ ID NO 12
<211> LENGTH: 7
<212> TYPE: PRT
<213> ORGANISM: Homo sapiens

<400> SEQUENCE: 12

Gln Gln Tyr His Ala His Pro
1               5

<210> SEQ ID NO 13
<211> LENGTH: 5
<212> TYPE: PRT
<213> ORGANISM: Homo sapiens

<400> SEQUENCE: 13

Ser Tyr Ala Ile Ser

```
<210> SEQ ID NO 14
<211> LENGTH: 10
<212> TYPE: PRT
<213> ORGANISM: Homo sapiens

<400> SEQUENCE: 14

Ile Ile Pro Ile Phe Gly Ala Ala Asn Pro
1               5                   10

<210> SEQ ID NO 15
<211> LENGTH: 6
<212> TYPE: PRT
<213> ORGANISM: Homo sapiens

<400> SEQUENCE: 15

Met Gly Arg Gly Lys Val
1               5

<210> SEQ ID NO 16
<211> LENGTH: 14
<212> TYPE: PRT
<213> ORGANISM: Homo sapiens

<400> SEQUENCE: 16

Gln Ser Val Leu Tyr Ser Pro Asn Asn Lys Asn Tyr Leu Ala
1               5                   10

<210> SEQ ID NO 17
<211> LENGTH: 5
<212> TYPE: PRT
<213> ORGANISM: Homo sapiens

<400> SEQUENCE: 17

Trp Ala Ser Thr Arg
1               5

<210> SEQ ID NO 18
<211> LENGTH: 7
<212> TYPE: PRT
<213> ORGANISM: Homo sapiens

<400> SEQUENCE: 18

Gln Gln Tyr Tyr Gly Ser Pro
1               5

<210> SEQ ID NO 19
<211> LENGTH: 5
<212> TYPE: PRT
<213> ORGANISM: Homo sapiens

<400> SEQUENCE: 19

Ser Tyr Gly Ile Asn
1               5

<210> SEQ ID NO 20
<211> LENGTH: 10
<212> TYPE: PRT
<213> ORGANISM: Homo sapiens

<400> SEQUENCE: 20

Ile Ser Ala Tyr Asn Gly Asn Thr Tyr Tyr
1               5                   10
```

```
<210> SEQ ID NO 21
<211> LENGTH: 9
<212> TYPE: PRT
<213> ORGANISM: Homo sapiens

<400> SEQUENCE: 21

Asp Leu Gly Gly Tyr Gly Ser Gly Ser
1               5

<210> SEQ ID NO 22
<211> LENGTH: 8
<212> TYPE: PRT
<213> ORGANISM: Homo sapiens

<400> SEQUENCE: 22

Gln Ser Val Ser Ser Asn Leu Ala
1               5

<210> SEQ ID NO 23
<211> LENGTH: 5
<212> TYPE: PRT
<213> ORGANISM: Homo sapiens

<400> SEQUENCE: 23

Gly Ala Ser Thr Arg
1               5

<210> SEQ ID NO 24
<211> LENGTH: 8
<212> TYPE: PRT
<213> ORGANISM: Homo sapiens

<400> SEQUENCE: 24

Gln Asp Tyr Arg Thr Trp Pro Arg
1               5
```

DOSAGE AND ADMINISTRATION OF ANTI-EGFR THERAPEUTICS

CROSS REFERENCE TO RELATED APPLICATIONS

This application is a continuation of International Application No. PCT/US2015/030870, filed on May 14, 2015, which claims priority to, and the benefit of, U.S. Application No. 61/996819, filed on May 14, 2014, and U.S. Application No. 62/005401, filed on May 30, 2014. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Sep. 28, 2015, is named MMJ-046PC-CN_SL.txt and is 9,916 bytes in size.

BACKGROUND

Appropriate dosing of parenteral medications such as antibody preparations is a critical factor in their administration to patients. One aspect of the requirement for safe and effective dosing schemes is that infusion reactions are occasionally associated with administration of antibody preparations to patients. In the field of anticancer therapy, infusion reactions have been reported in association with the administration of several antibody-targeted therapeutics, including rituximab, trastuzumab, bevacizumab, cetuximab and panitumumab. Such infusion reactions include chills, pyrexia and dizziness, which are often associated with hypersensitivity and allergic symptoms such as urticaria. Severe infusion reactions may be life-threatening and include anaphylactoid symptoms such as dyspnea, bronchospasm, hypotension, loss of consciousness and shock, or even myocardial infarction or cardiac arrest in some patients. Infusion related reactions are assigned grades according to the National Cancer Institute Common Terminology Criteria for Adverse Events (Version 4.0) as follows. Grade 1 includes a mild transient reaction, wherein interruption of infusion and/or interventions is not indicated. Grade 2 includes reactions that indicate the therapy or infusion should be interrupted, but the reaction responds promptly to symptomatic treatment (e.g., NSAIDS, narcotics, or intravenous (i.v.) fluids). In such cases, prophylactic medications are indicated for up to 24 hours at the discretion of the physician or staff. Grade 3 reactions include prolonged infusion related reactions (e.g., reactions not rapidly responsive to symptomatic medication and/or a brief interruption of infusion), a recurrence of symptoms following initial improvement, and hospitalization indicated for clinical sequelae. Grade 4 includes infusion related reactions with life-threatening consequences, and urgent intervention indicated as well as cessation of infusion. Grade 5 includes infusion related reactions causing the death of the patient.

Anti-EGFR antibodies provide beneficial therapy for various cancers, but may be ineffective or lose effectiveness over time. Newer EGFR inhibitory antibody preparations are in development, including oligoclonal mixtures of anti-EGFR monoclonal antibodies. Oligoclonal anti-EGFR antibody mixtures represent a recent advance in anti-EGFR cancer therapy and have been shown preclinically to provide superior anti-cancer therapeutic effects. MM-151 and Sym004 are oligoclonal mixtures of antibodies that bind to the extracellular domain of EGFR and inhibit EGFR activity. MM-151 comprises a formulation in a pharmaceutically acceptable carrier of a triple combination of monoclonal antibody P1X, monoclonal antibody P2X, and monoclonal antibody P3X at a P1X:P2X:P3X molar ratio of 2:2:1. These experimental therapies are designed to be more potent than first generation anti-EGFR monoclonal antibodies, and thus require specially adapted dosing and administration schedules and procedures.

Thus, there is an unmet need to develop and implement methods of safely and effectively administering novel antibody-comprising therapeutics, including methods for preventing and ameliorating infusion reactions in patients, e.g., cancer patients receiving such therapeutics. The following disclosure provides such methods and confers additional advantages.

SUMMARY

Disclosed herein are compositions and methods designed to safely and effectively administer oligoclonal anti-EGFR antibody preparations such as MM-151 and Sym004 and to prevent and ameliorate infusion reactions in patients receiving treatment such antibody-based therapeutics.

In one aspect, a method is provided for treating a cancer in a human patient by administering an oligoclonal mixture of anti-EGFR antibodies to the patient, wherein the method comprises intravenously administering the oligoclonal mixture of anti-EGFR antibodies in at least one treatment cycle, the at least one cycle comprising:

an initial two week treatment cycle consisting of a first week and a second week, wherein a first dose of the an oligoclonal mixture of anti-EGFR antibodies is administered during the first week administered at a rate of X mg/hour for a first ½ hour, immediately followed by a rate of 2X mg/hour for a second ½ hour, immediately followed by a rate of 4X mg/hour until all of the first dose has been administered and a second dose, that is greater than or equal to the first dose, is administered during the second week; wherein administration, at each rate subsequent to the first ½ hour, is optionally one or more of: delayed, altered or not carried out if the patient exhibits an adverse reaction to the administration at the preceding rate. In one embodiment, if the patient exhibits an adverse reaction to the administration of the anti-EGFR antibodies at the preceding rate (i.e., the rate at which the adverse reaction was observed) and the alteration comprises an interruption of administration, i) the patient is treated for symptoms of the adverse reaction at the discretion of an attending clinician, and ii) following treatment of the symptoms, the administration is resumed at a rate lower than or equal to the rate at which the administration was interrupted. In one embodiment, the administration is resumed at half the rate at which the administration was interrupted.

In another formulation of this aspect, provided herein is use of an oligoclonal mixture of anti-EGFR antibodies (for the manufacture of a medicament) for treating a cancer in a human patient by intravenous administration of the medicament to the patient in at least one treatment cycle, the at least one cycle comprising: an initial two week treatment cycle consisting of a first week and a second week, wherein a first dose of the an oligoclonal mixture of anti-EGFR antibodies is administered during the first week administered at a rate of X mg/hour for a first ½ hour, immediately followed by a rate of 2X mg/hour for a second ½ hour, immediately followed by a rate of 4X mg/hour until all of the first dose has been administered and a second dose, that is greater than or equal to the first dose, is administered during the second week.

In one embodiment, the second dose is administered at a rate of X mg/hour for a first ½ hour, immediately followed by a rate of 2X mg/hour for a second ½ hour, immediately followed by a rate of 4X mg/hour for a third ½ hour, immediately followed by a rate of 8X mg/hour until all of the second dose has been administered, wherein administration at each rate of the second dose is optionally either delayed or not carried out if the patient exhibits an adverse reaction to the administration at the preceding rate or of the preceding dose.

In another embodiment, if the patient tolerates the initial cycle, the at least one cycle further comprises at least one subsequent treatment cycle, each treatment cycle comprising at least one administration of the oligoclonal mixture of anti-EGFR antibodies at a third dose. In another embodiment, the third dose is greater than or equal to the second dose and is greater than the first dose.

In another embodiment, if the third dose of the oligoclonal mixture of anti-EGFR antibodies is administered, it is administered at a rate of 2X mg/hour for a first ½ hour, immediately followed by a rate of 4X mg/hour for a second ½ hour, immediately followed by a rate of 8X mg/hour for a third ½ hour, immediately followed by a rate of 16X mg/hour until all of the third dose has been administered. In one embodiment, X is 25.

In one embodiment, the first dose of the oligoclonal mixture of anti-EGFR antibodies is about 225 mg or is about 3 mg/kg. In another embodiment, the second dose is about 450 mg or is about 6 mg/kg.

In one embodiment, the at least one subsequent treatment cycle is three weeks or four weeks.

In another embodiment, the at least one subsequent treatment cycle is four weeks, and, if administered, the third dose is administered on day 1 of each week of the four week treatment cycle. In yet another embodiment, the at least one subsequent treatment cycle is four weeks, and, if administered, the third dose is administered during the first week and the third week of each four week cycle.

In one embodiment, the at least one subsequent treatment cycle is three weeks, and, if administered, the third dose of the oligoclonal mixture of anti-EGFR antibodies is administered during week 1 of each three week cycle. In another embodiment, the oligoclonal mixture of anti-EGFR antibodies consists of two or more anti-EGFR antibodies.

In one embodiment, the oligoclonal mixture of anti-EGFR antibodies consists of anti-EGFR antibodies that specifically bind to two or more different epitopes of the extracellular domain of EGFR.

In one embodiment, the two or more different epitopes is three different epitopes.

In one embodiment, the two or more anti-EGFR antibodies is three anti-EGFR antibodies. In another embodiment, the three anti-EGFR antibodies is MM-151bio or optionally MM-151. In yet another embodiment, the three anti-EGFR antibodies comprise a first antibody with a heavy chain comprising SEQ ID NO:1 and a light chain comprising SEQ ID NO:2; a second antibody with a heavy chain comprising SEQ ID NO:3 and a light chain comprising SEQ ID NO:4; and a third antibody with a heavy chain comprising SEQ ID NO:5 and a light chain comprising SEQ ID NO:6. In another embodiment, the three anti-EGFR antibodies comprise a first antibody comprising heavy chain CDRs 1, 2 and 3 set forth in SEQ ID NOs: 7, 8 and 9 respectively, and light chain CDRs 1, 2 and 3 set forth in SEQ ID NOs: 10, 11 and 12 respectively; a second antibody comprising heavy chain CDRs 1, 2 and 3 set forth in SEQ ID NOs: 13, 14 and 15 respectively, and light chain CDRs 1, 2 and 3 set forth in SEQ ID NOs: 16, 17, and 18 respectively; and a third antibody comprising heavy chain CDRs 1, 2 and 3 set forth in SEQ ID NOs: 19, 20 and 21 respectively, and light chain CDRs 1, 2 and 3 set forth in SEQ ID NOs: 22, 23 and 24 respectively.

In another embodiment, the antibodies are IgG antibodies, optionally IgG1 antibodies.

In another embodiment, the third dose (and optionally each subsequent dose) of the oligoclonal mixture of anti-EGFR antibodies is about 4.5 mg/kg, about 6 mg/kg, about 7.5 mg/kg, about 9 mg/kg, about 10 mg/kg, about 10.5 mg/kg, about 11 mg/kg, about 12 mg/kg, about 13 mg/kg, about 14 mg/kg, about 15 mg/kg, about 18 mg/kg, or about 20 mg/kg, and is administered weekly, bi-weekly or tri-weekly. In one embodiment, the third dose of the oligoclonal mixture of anti-EGFR antibodies is 10.5 mg/kg. In one embodiment, the 10.5 mg/kg is administered weekly.

In another aspect, provided are methods for treating a patient having a cancer, comprising co-administration of a topoisomerase inhibitor and the oligoclonal mixture of anti-EGFR antibodies. In one embodiment, the at least one dose of a topoisomerase inhibitor is administered at least during the initial two week treatment cycle, optionally wherein, if the patient tolerates the initial cycle, the at least one cycle further comprises at least one subsequent treatment cycle, each subsequent treatment cycle comprising at least one administration of the oligoclonal mixture of anti-EGFR antibodies at a third dose. In one embodiment, the topoisomerase inhibitor is administered during the initial two week treatment cycle prior to administration of the oligoclonal mixture of anti-EGFR antibodies. In another embodiment, the topoisomerase inhibitor is additionally administered during the at least one subsequent treatment cycle, and during each subsequent cycle is coadministered prior to administration of the oligoclonal mixture of anti-EGFR antibodies.

In one embodiment, the topoisomerase inhibitor is a topoisomerase I inhibitor. In one embodiment, the topoisomerase I inhibitor is a camptothecin. In one embodiment, the camptothecin is irinotecan HCl or liposomal irinotecan (e.g., liposomal irinotecan sucrosofate).

In one embodiment, each cycle of the at least one subsequent treatment cycle is a four week treatment cycle and the third dose of the oligoclonal mixture of anti-EGFR antibodies and the topoisomerase inhibitor are each administered during day one of week one and day one of week three of the four week treatment cycle, optionally wherein, in each cycle of co-administration, the topoisomerase inhibitor is administered prior to administration of the oligoclonal mixture of anti-EGFR antibodies. In another embodiment, each cycle of the at least one subsequent treatment cycle is a four week treatment cycle and the topoisomerase inhibitor is administered on day one of week one of each four week treatment cycle and the anti-EGFR inhibitor is administered weekly. In one embodiment, in each cycle of co-administration, the topoisomerase inhibitor is administered prior to administration of the oligoclonal mixture of anti-EGFR antibodies.

In one aspect, provided is a method for ameliorating and/or preventing infusion reactions in a patient having a cancer comprising administering to the patient anti-inflammatory treatments prior to administering an oligoclonal mixture of anti-EGFR antibodies and/or irinotecan. Such method comprises a pretreatment comprising an effective amount of each of 1) drug 1: a histamine H1 blocker; and one or both of: 2) drug 2: an anti-inflammatory steroid; and 3) drug 3: acetaminophen, which is administered to the patient. In one embodiment, the one or both of 2) and 3) are both of 2) and 3); which pretreatment is administered to the patient prior to each infusion of the oligoclonal mixture of anti-EGFR antibodies. In another embodiment, the effective amount of each of 1) and one or both of 2) and 3) are all administered to the patient 30-60 minutes prior to the administration of the oligoclonal mixture of anti-EGFR antibodies. In one embodiment, 2) is dexamethasone or methylprednisolone. In another embodiment, the dexamethasone is administered to the patient at a dose of 5, 10, 15, 20 or 25 mg, or the methylprednisolone is administered to the patient at a dose of 25, 50, 75, 100, or 125 mg. In one embodiment, 2) is methylprednisolone. In another embodiment, 1) is diphenhydramine. In another embodiment, the diphenhydramine is administered at a dose of 25 mg to 50 mg. In one embodiment, the 25 mg to 50 mg is 25 mg or 50 mg.

In one embodiment, if the patient develops an infusion reaction in response to a cycle of administration of the oligoclonal mixture of anti-EGFR antibodies, an effective amount of 1) and/or 2) and/or 3) is re-administered during the cycle. In one embodiment, an effective amount of one or both of 1) and 2) is re-administered when the infusion reaction is observed. In some embodiments, administration of the anti-EGFR antibodies may be interrupted while the effective amount of 2) is re-administered, and then resumed when 2) has been administered. In another embodiment, the administration of the pretreatment is repeated prior to each subsequent cycle.

In various embodiments, treatment of the patient in accordance with the disclosed methods results in a response classified as PR or CR, or in an SD response.

DETAILED DESCRIPTION

Figure 1A:
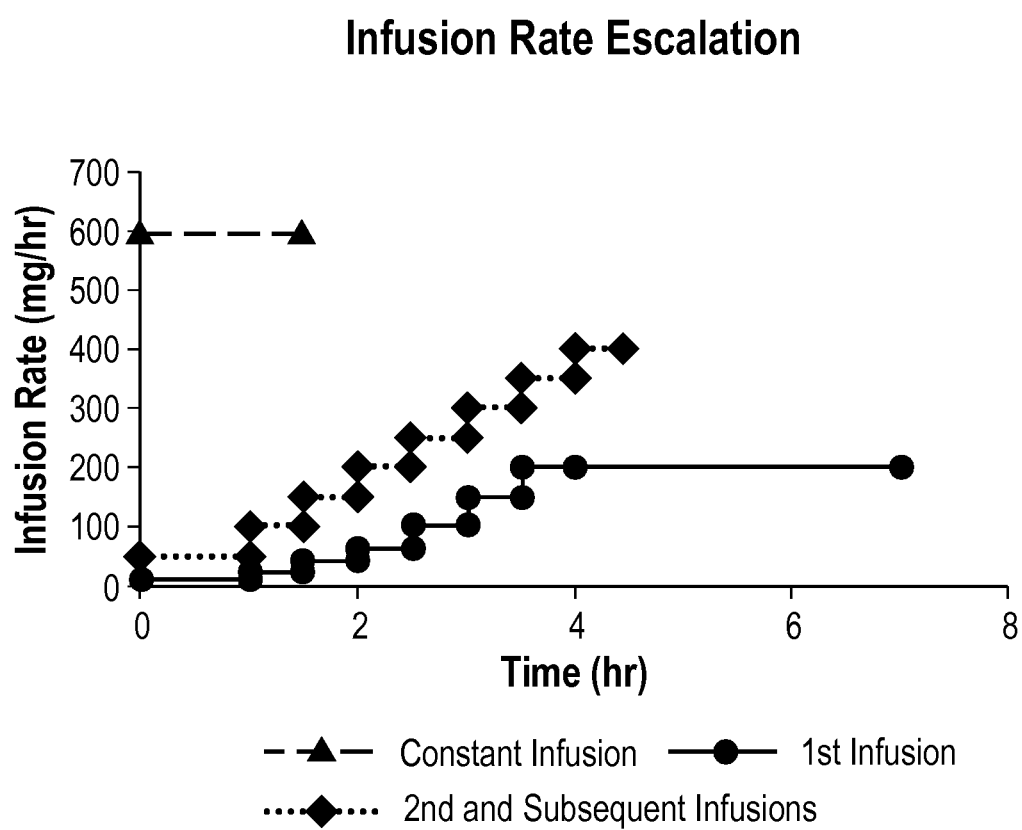
FIG. 1A is a graphic representation of the changes in infusion rate associated with the data set forth in Table III and Table IV plotted in comparison to constant infusion.

Oligoclonal anti-EGFR antibody mixtures represent a recent advance in anti-EGFR cancer therapy. MM-151 and Sym004 (SYMPHOGEN) are each oligoclonal mixtures of antibodies that bind to the extracellular domain of EGFR and inhibit EGFR activity. MM-151 comprises a formulation in a pharmaceutically acceptable carrier of a triple combination of P1X +P2X +P3X at a P1X:P2X:P3X molar ratio of 2:2:1. While MM-151 comprises P1X, P2X and P3X, variants of P1X, P2X and P3X have been prepared that comprise $V_H$ and $V_L$ sequences closely related to those of SEQ ID NOs 1-6; see, e.g., U.S. patent publications Nos. 20110287002 and 20140127207. Related variants may preserve a sufficient degree of functional similarity to provide bioequivalent pharmacokinetics, safety and efficacy. Closely related variants of P1X $V_H$ and $V_L$, P2X $V_H$ and $V_L$, and P3X $V_H$ and $V_L$ may each include one, two or all three of the complementarity determining regions (CDRs) of each variable region. Such variants may be combined (e.g., at a P1X analog:P2X analog:P3X analog molar ratio of about 2:2:1 in a pharmaceutically acceptable carrier), and, where closely enough related to P1X, P2X and P3X, may thereby form a variant preparation biosimilar to MM-151. As used in this specification, and in the claims, "MM-151bio" is meant to include MM-151 and such MM-151 biosimilar preparations.

Provided herein are methods for treating a cancer with an anti-EGFR antibody therapeutic. In particular, disclosed herein are specific dosages and regimens for administering an oligoclonal anti-EGFR antibody therapeutic preparation to a human patient having a cancer, such dosages and regimens being designed to increase a patient's tolerance of the therapeutic, decrease the likelihood of infusion-related reactions (IRRs), and maximize the amount of dose that may be administered to the patient safely so at to safely achieve maximum anti-cancer benefits. Previous attempts to mitigate IRR cause by administration of antibody-based anti-EGFR therapeutics have resulted in very long infusion times, e.g., 6-9 hours in some cases, depending on body weight. Infusion times longer than 5 hours may be impractical in a clinical setting. Other attempts to address infusion reactions require patients to come to the clinic for treatment two or more days in a row. In order to avoid these difficulties, a regimen was designed that reduces or prevents infusion reactions, avoids long infusions, and avoids split-day treatments, thus allowing administration of higher doses of oligoclonal anti-EGFR therapy to patients, which higher doses may provide more effective therapy.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, human antibodies may be administered once or twice weekly by intravenous injection or once or twice monthly by intravenous injection.

It is especially advantageous to formulate parenteral compositions in unit dosage form for ease of administration and uniformity of dosage. Unit dosage form as used herein refers to physically discrete units suited as unitary dosages for the subjects to be treated; each unit contains a predetermined quantity of antibodies, e.g., a quantity calculated to provide an amount sufficient for a single cycle of administration.

Oligoclonal Antibody Mixtures

P1X is a human IgG1 having a heavy chain variable region ($V_H$) comprising SEQ ID NO: 1 and a light chain variable region ($V_L$) comprising SEQ ID NO: 2;

P2X is a human IgG1 having a $V_H$ comprising SEQ ID NO: 3 and a $V_L$ comprising SEQ ID NO: 4; and P3X is a human IgG1 having a $V_H$ comprising SEQ ID NO: 5 and a $V_L$ comprising SEQ ID NO: 6.

In various embodiments, P1X, P2X and P3X are each expressed in recombinant cell protein expression systems. Such protein expression systems include commercially available systems using bacterial cells (e.g., *E. coli* with PET vector), insect cells (e.g., Sf9 cells with pIB/V5-Histadine vector) and mammalian cells (e.g., HEK 293 cells with pLOC vector). A preferred expression host cell is a Chinese hamster ovary (CHO) cell. A preferred expression vector is a commercially available mammalian expression vector that is suitable for expression of IgG heavy and light chains in a CHO cell, e.g., one from SELEXIS, LONZA, or GE HEALTHCARE.

TABLE I

Exemplary Antibody Variable Regions

| P1X $V_H$ | MGFGLSWLFLVAILKGVQCQ VQLVQSGAEVKKPGSSVKVS CKASGGTFSSYAISWVRQAP GQGLEWMGSIIPIFGTVNYA QKFQGRVTITADESTSTAYM ELSSLRSEDTAVYYCARDPS VNLYWYFDLWGRGTLVTSS | SEQ ID NO: 1 |
|---|---|---|
| P1X $V_L$ | MGTPAQLLFLLLLWLPDTTG DIQMTQSPSTLSASVGDRVT ITCRASQSISSWWAWYQQKP GKAPKLLIYDASSLESGVPS RFSGSGSGTEFTLTISSLQP DDFATYYCQQYHAHPTTFGG GTKVEIK | SEQ ID NO: 2 |
| P2X $V_H$ | MGFGLSWLFLVAILKGVQCQ VQLVQSGAEVKKPGSSVKVS CKASGGTFGSYAISWVRQAP GQGLEWMGSIIPIFGAANPA QKSQGRVTITADESTSTAYM ELSSLRSEDTAVYYCAKMGR GKVAFDIWGQGTMVTVSS | SEQ ID NO: 3 |
| P2X $V_L$ | MGTPAQLLFLLLLWLPDTTG DIVMTQSPDSLAVSLGERAT INCKSSQSVLYSPNNKNYLA WYQQKPGQPPKLLIYWASTR ESGVPDRFSGSGSGTDFTLT ISSLQAEDVAVYYCQQYYGS PITFGGGTKVEIK | SEQ ID NO: 4 |
| P3X $V_H$ | MGFGLSWLFLVAILKGVQCQ VQLVQSGAEVKKPGASVKVS CKASGYAFTSYGINWVRQAP GQGLEWMGWISAYNGNTYYA QKLRGRVTMTTDTSTSTAYM ELRSLRSDDTAVYYCARDLG GYGSGSVPFDPWGQGTLVTV SS | SEQ ID NO: 5 |
| P3X $V_L$ | MGTPAQLLFLLLLWLPDTTG EIVMTQSPATLSVSPGERAT LSCRASQSVSSNLAWYQQKP GQAPRLLIYGASTRATGIPA RFSGSGSGTEFTLTISSLQS EDFAVYYCQDYRTWPRRVFG GGTKVEIK | SEQ ID NO: 6 |

TABLE II

Exemplary Antibody CDRs

| P1X $V_H$CDR1 | SYAIS | SEQ ID NO: 7 |
|---|---|---|
| P1X $V_H$CDR2 | IIPIFGTVNY | SEQ ID NO: 8 |
| P1X $V_H$CDR3 | DPSVNL | SEQ ID NO: 9 |
| P1X $V_L$CDR1 | QSISSWWA | SEQ ID NO: 10 |
| P1X $V_L$CDR2 | DASSL | SEQ ID NO: 11 |
| P1X $V_L$CDR3 | QQYHAHP | SEQ ID NO: 12 |
| P2X $V_H$CDR1 | SYAIS | SEQ ID NO: 13 |
| P2X $V_H$CDR2 | IIPIFGAANP | SEQ ID NO: 14 |
| P2X $V_H$CDR3 | MGRGKV | SEQ ID NO: 15 |
| P2X $V_L$CDR1 | QSVLYSPNNKNYLA | SEQ ID NO: 16 |
| P2X $V_L$CDR2 | WASTR | SEQ ID NO: 17 |
| P2X $V_L$CDR3 | QQYYGSP | SEQ ID NO: 18 |
| P3X $V_H$CDR1 | SYGIN | SEQ ID NO: 19 |
| P3X $V_H$CDR2 | ISAYNGNTYY | SEQ ID NO: 20 |
| P3X $V_H$CDR3 | DLGGYGSGS | SEQ ID NO: 21 |
| P3X $V_L$CDR1 | QSVSSNLA | SEQ ID NO: 22 |
| P3X $V_L$CDR2 | GASTR | SEQ ID NO: 23 |
| P3X $V_L$CDR3 | QDYRTWPR | SEQ ID NO: 24 |

Dosage of Oligoclonal Antibody Mixtures

In one embodiment, the oligoclonal antibody mixture is formulated for intravenous administration. In particular embodiments, the oligoclonal antibody mixture is administered at a dose selected from: priming doses of from 100 to 1000 mg, e.g., 225 mg or 450 mg, or 3 mg/kg or 6 mg/kg; and full doses of from 1 to 20 mg/kg, e.g., 3 mg/kg, 6 mg/kg, 7.5 mg/kg, 9 mg/kg, 10.5 mg/kg, 12 mg/kg, 15 mg/kg or 18 mg/kg or 20 mg/kg. In one embodiment, the dose of the oligoclonal antibody mixture is varied over time. For example, the antibody may be initially administered at a low dose and increased over time.

Camptothecin Topoisomerase I Inhibitors

Irinotecan hydrochloride (HCl) is marketed as CAMPTOSAR® (irinotecan hydrochloride injection). Irinotecan is an antineoplastic agent of the topoisomerase I inhibitor class that is a derivative of camptothecin, an alkaloid extract from plants such as *Camptotheca acuminate*. Camptothecin and its derivatives are referred to as camptothecins, and irinotecan is a camptothecin. The chemical name for irinotecan is (S)-4,11-diethyl-3,4,12,14-tetrahydro-4-hydroxy-3,14-dioxolH pyrano [3',4':6,7]-indolizino[1,2-b]quinolin-9-yl-[1,4'bipiperidine]-1'-carboxylate. Irinotecan HCl is a monohydrochloride trihydrate that is a pale yellow to yellow crystalline powder, with the empirical formula $C_{33}H_{38}N_4O_6 \cdot HCl \cdot 3H_2O$ and a molecular weight of 677.19. It is slightly soluble in water and organic solvents. Irinotecan HCl is also known as CPT-11. Other camptothecin topoisomerase I inhibitors include 9-aminocamptothecin, 7-ethylcamptothecin, 10-hydroxycamptothecin, 9-nitrocamptothecin, 10,11-methylenedioxycamptothecin, 9-amino-10,11-methylenedioxycamptothecin, 9-chloro-10,11-methylenedioxycamptothecin, irinotecan, topotecan, lurtotecan, silatecan, (7-(4-methylpiperazinomethylene)-10,11-ethylenedioxy-20(S)-camptothecin, 7-(4-methylpiperazinomethylene)-10,11-methylenedioxy-20(S)-camptothecin and 7-(2-N-isopropylamino)ethyl)-(20S)-camptothecin.

Pharmaceutical Compositions

Pharmaceutical compositions suitable for administration to a patient are typically in forms suitable for parenteral administration, e.g., in a liquid carrier, or suitable for reconstitution into liquid solution or suspension, for intravenous administration.

In general, compositions typically comprise a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans. The term "carrier" refers to a diluent, adjuvant, excipient, or vehicle with which the antibodies are administered. Such pharmaceutical carriers can be sterile liquids, typically water and aqueous solutions such as saline and aqueous sucrose or dextrose and glycerol solutions, which may also contain excipients such as emulsifiers (e.g., a polysorbate), buffering agents (e.g. phosphate buffers or amino acids). Liquid compositions for parenteral administration can be formulated for administration by injection or continuous infusion. Routes of administration by injection or infusion include intravenous, intraperitoneal, intramuscular, intrathecal and subcutaneous. In one embodiment, an oligoclonal mixture of anti-EGFR antibodies and irinotecan are administered intravenously (e.g., separately or together, each, e.g., for MM-151, over the course of 60, 90, 120, 150, 180, 210, 240, 270, 300, 330, or 360 minutes).

MM-151 may be formulated for intravenous infusion as a clear liquid that may be supplied in sterile, single-use vials containing 10 mL of MM-151 (with an extractable volume of 9.5 mL) at a total protein concentration of 25 mg/mL in 20 mM histidine, 10% sucrose, 0.02% polysorbate 80, pH 6.0. MM-151 Drug Product thus formulated should be stored at 2-8° C.

Irinotecan HCl is supplied as a sterile, pale yellow, clear, aqueous solution. It is available in two single-dose sizes in brown glass vials: 2 mL-fill vials contain 40 mg irinotecan hydrochloride and 5 mL-fill vials contain 100 mg irinotecan hydrochloride. Irinotecan is also available in three single-dose sizes in amber-colored polypropylene CYTOSAFE vials: 2 mL-fill vials contain 40 mg irinotecan hydrochloride, 5 mL-fill vials contain 100 mg irinotecan hydrochloride and 15 mL-fill vials contain 300 mg irinotecan hydrochloride. Each milliliter of solution contains 20 mg of irinotecan hydrochloride (on the basis of the trihydrate salt), 45 mg of sorbitol, NF, and 0.9 mg of lactic acid, USP. The pH of the solution has been adjusted to 3.5 (range, 3.0 to 3.8) with sodium hydroxide or hydrochloric acid. Irinotecan is intended for dilution with 5% Dextrose Injection, USP (D5W), or 0.9% Sodium Chloride Injection, USP, prior to intravenous infusion. The preferred diluent is 5% Dextrose Injection, USP.

Patient Populations

Provided herein are effective methods for treating solid tumors (e.g., that are advanced and/or EGFR dependent) in a human patient using an oligoclonal mixture of anti-EGFR antibodies, or using a combination of such an oligoclonal mixture and irinotecan.

In one embodiment, a human patient for treatment of a cancer in accordance with the methods provided herein has not been previously been treated for the cancer with an antineoplastic medication. In another embodiment, a human patient for treatment using the subject methods and compositions has evidence of recurrent or persistent disease following primary chemotherapy. In one embodiment, the human patient suffers from colorectal cancer, head and neck cancer (e.g., head and neck squamous cell carcinoma), non-small cell lung cancer, gastric cancer, breast cancer, endometrial cancer, ovarian cancer, cervical cancer, bladder cancer (and related urothelial cancers), esophageal cancer, brain cancer (e.g., glioblastoma multiforme) liver cancer (e.g., hepatoma), pancreatic cancer, and squamous cell carcinoma. In one embodiment, the patient has a pathologically documented, definitively diagnosed colorectal adenocarcinoma that is locally advanced or metastatic and surgically unresectable.

In another embodiment, a patient has shown evidence of recurrent or persistent disease following treatment with at least 1 and no more than 2 treatment regimens for locally advanced or metastatic disease. In one embodiment, if the patient is to receive combination therapy comprising irinotecan, the patient should have received only 1 prior treatment containing irinotecan.

In one embodiment, patients must have received no prior therapy with EGFR-targeted therapeutics. In another embodiment, patients must have received prior therapy with one or more EGFR-targeted therapeutics and have become refractory to such therapy.

Combination Therapies

The methods provided herein are useful for both anti-EGFR monotherapy and combination therapy with other anti-cancer therapies, e.g. chemotherapeutics (e.g., irinotecan, 5-FU/leucovorin, oxaliplatin (and combinations of the foregoing such as FOLFOX and FOLFIRI), MM-398 (alone or in combination with 5-FU/leucovorin), targeted small molecules, e.g., trametinib, selumetinib, binimetinib, cobimetinib, afatinib, sunitinib, sorafinib, pazopanib, imatinib, vemurafinib, dabrafenib, erlotinib, gefitinib, and lapatinib, or monoclonal antibodies such as seribantumab, MM-141, MM-131, MM-111, ipilimumab, nivolumab, pembrolizumab, pidilizumab, trastuzumab, pertuzumab, ado-trastuzumab emtansine. Each of these anti-cancer therapies is preferably co-administered at the manufacturer's recommended dose, unless such a dose causes an adverse reaction when administered in combination with MM-151 (or MM-151bio), in which case a reduced dose is preferred.

In one embodiment, an oligoclonal mixture of anti-EGFR antibodies is administered concomitantly with irinotecan, to effect improvement in subjects having a solid tumor. In one embodiment, the oligoclonal mixture of anti-EGFR antibodies is MM-151 or MM-151bio.

As used herein, adjunctive or combined administration (co-administration) includes simultaneous administration of the compounds in the same or different dosage form, or separate administration of the compounds (e.g., sequential administration). For example, the oligoclonal antibody mixture can be simultaneously administered with irinotecan, wherein both the antibody and the irinotecan are formulated together. Alternatively, the oligoclonal antibody mixture can be administered in combination with irinotecan, wherein both the antibody mixture and the irinotecan are formulated for separate administration and are administered concurrently or sequentially. For example, the irinotecan can be administered first followed by (e.g., immediately followed by) the administration of the oligoclonal antibody mixture, or vice versa.

Such concurrent or sequential administration beneficially results in both the oligoclonal antibody mixture and irinotecan being simultaneously present in treated patients.

In one embodiment, the oligoclonal antibody mixture is administered as a monotherapy prior to the combination therapy. In another embodiment, the oligoclonal antibody mixture is administered as a monotherapy following the combination therapy.

Outcomes

Responses to therapy may include:

Complete Response (CR): Disappearance of all target lesions. Any pathological lymph nodes (whether target or non-target) must have reduction in short axis to <10 mm;

Partial Response (PR): At least a 30% decrease in the sum of the diameters of target lesions, taking as reference the baseline sum diameters;

Progressive Disease (PD): At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression); and Stable Disease (SD): Neither sufficient shrinkage to qualify for PR nor sufficient increase to qualify for PD, taking as reference the smallest sum diameters while on study. A change of 20% or less that does not increase the sum of the diameters by 5 mm or more is coded as stable disease. To be assigned a status of stable disease, measurements must have met the stable disease criteria at least once after study entry at a minimum interval of 6 weeks.

In exemplary outcomes, patients treated according to the methods disclosed herein may experience improvement in at least one sign of cancer. In one embodiment, the patient so treated exhibits CR, PR; in another embodiment the patient exhibits SD.

In another embodiment, the patient so treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, such improvement is measured by a reduction in the quantity and/or size of measurable tumor lesions. Measurable lesions are defined as those that can be accurately measured in at least one dimension (longest diameter is to be recorded) as ≥10 mm by CT scan (CT scan slice thickness no greater than 5 mm), 10 mm caliper measurement by clinical exam or >20 mm by chest X-ray. The size of non-target lesions, e.g., pathological lymph nodes can also be measured for improvement. In one embodiment, lesions can be measured on chest x-rays or CT or MRI films.

In other embodiments, cytology or histology can be used to evaluate responsiveness to a therapy. The cytological confirmation of the neoplastic origin of any effusion that appears or worsens during treatment when the measurable tumor has met criteria for response or stable disease can be considered to differentiate between response or stable disease (an effusion may be a side effect of the treatment) and progressive disease.

In some embodiments, administration of effective amounts of the oligoclonal anti-EGFR antibody mixture, e.g., MM-151 or MM-151bio, and optionally irinotecan according to any of the methods provided herein produce at least one therapeutic effect selected from the group consisting of reduction in size of a tumor, reduction in number of metastatic lesions appearing over time, complete remission, partial remission, stable disease, increase in overall response rate, or a pathologic complete response. In some embodiments, the provided methods of combination treatment produce a comparable clinical benefit rate (CBR=CR+PR+SD≥6 months) better than that achieved by the oligoclonal anti-EGFR antibody mixture, e.g., MM-151 or MM-151bio, or irinotecan alone, or the combination of cetuximab and irinotecan. In other embodiments, the improvement of clinical benefit rate is about 10% 20%, 30%, 40%, 50%, 60%, 70%, 80%, 90%, or more compared to cetuximab or irinotecan alone or the combination of cetuximab and irinotecan.

Kits and Unit Dosage Forms

Also provided are kits that include a pharmaceutical composition containing an oligoclonal mixture of anti-EGFR antibodies, such as MM-151 or MM-151bio, and a pharmaceutically-acceptable carrier, in a therapeutically effective amount adapted for use in the preceding methods.

The kits can optionally also include instructions, e.g., comprising administration parameters including dosages and infusion rates, to allow a practitioner (e.g., a physician, nurse, or patient) to administer the composition contained therein to a patient having cancer in accordance with the methods disclosed herein. In one embodiment, the kit further comprises irinotecan. Optionally, the kit may comprise a preparation of oligoclonal anti-EGFR antibodies (e.g., MM-151, MM-151bio or Sym004) and/or irinotecan in a desired unit dosage form for administration.

Pretreatments

Prior to infusion of oligoclonal anti-EGFR antibodies (e.g., 30-60 minutes before each infusion), one or more drugs may be administered to reduce the incidence and severity of infusion reactions. A histamine H1 antagonist (antihistamine) may be administered. Exemplary antihistamines for this pre-treatment include diphenhydramine, chlorpheniramine, and brompheniramine. In one embodiment, diphenhydramine is administered orally (p.o.) or intravenously (i.v.) at a dose of 25-50 mg. Acetaminophen may be administered, e.g., at a dose of 650 mg p.o. or i.v. Additionally, an anti-inflammatory steroid may be administered. Exemplary steroids for this purpose include dexamethasone and methylprednisolone. In one embodiment, methylprednisolone is administered intravenously (i.v.) at a dose of 25-125 mg (e.g., 25, 50, 75, 100, or 125 mg). In another embodiment, dexamethasone is administered p.o. or i.v. at a dose of 5-25 mg (e.g., 5, 10, 15, 20 or 25 mg). Pretreatment may optionally be reduced or discontinued after the first full dose (i.e., dose other than a priming dose) of oligoclonal anti-EGFR antibodies, particularly if no infusion reactions are observed. Pretreatment may optionally be resumed at a later dosing visit, particularly to reduce the incidence of infusion reactions in patients that did not receive drug on one or more preceding visits.

EXAMPLES

The present invention is further illustrated by the following Examples, which should not be construed as further limiting. These Examples incorporate results obtained during a Phase I clinical trial of MM-151. In this trial, patients who received a relatively high dose of MM-151 at the beginning of the first infusion were much more likely to develop a rapidly presenting infusion reaction (e.g., hypersensitivity) at the beginning of the dosing, requiring a stoppage in treatment, than were patients who received a relatively lower dose of MM-151. In addition, patients who received higher doses during the first infusion of MM-151 and didn't exhibit a hypersensitivity reaction tended to develop cytokine-driven infusion reactions about three to six hours after the beginning of the drug infusion. Finally, patients who received anti-inflammatory treatments prior to the first infusion of MM-151 exhibited fewer infusion reactions than patients who did not receive anti-inflammatory treatments prior to MM-151 infusion.

Surprisingly, patients were much less likely to develop an infusion reaction in subsequent infusions compared to the first infusion, indicating that patients experience fewer side effects with each subsequent administration of MM-151.

As presented in the tables below "FD" (full dose), may be, e.g., 4.5, 6, 7, 7.5, 8, 9, 10, 10.5, 11, 12, 13, 14, 15, 16, 17, 18, 19, or 20 mg/kg. In those Tables relating to combination therapy comprising irinotecan, "180" indicates 180 mg/m$^2$ of irinotecan HCl, which is preferably administered prior to MM-151 administration. The amounts of either or both of 1) each full dose of MM-151 or 2) of each full dose of the combination therapy, may be reduced during the course of treatment at the discretion of the treating physician, such as in response to an adverse event.

Example 1

Pre-Treatment

In all patients not treated with the Standard Schedule described below, premedication with methylprednisolone i.v. at a dose of 25-125 mg, diphenhydramine p.o. or i.v. at a dose of 25 or 50 mg, and acetaminophen p.o. or i.v. at a dose of 650 mg is administered to each patient prior to the initial infusion of MM-151 and premedication is preferably continued before each subsequent infusion of MM-151, but may be altered at the treating physician's discretion.

Example 2

A Priming Phase with Escalating Rate of Infusion and Subsequent Dosing for MM-151 Monotherapy Administration In the following clinical trial, the first 37 patients to be treated received MM-151 according to the Standard Schedule, i.e., by constant infusion (approximately 60-90 minutes in duration). These patients frequently exhibited infusion-related reactions that were sometimes severe. In some cases, administration of MM-151 to patients who exhibited infusion-related reactions was terminated prematurely and not restarted (i.e. the intended dose of MM-151 was not administered). In some cases, patients who exhibited infusion-related reactions were withdrawn from the trial due to the severity of their reactions. The trial design was then modified to enable the determination of whether MM-151 would be better tolerated with pre-medication and with modified infusion protocols involving administration via a slow first infusion, followed by increased rates on subsequent infusions. Two such modified infusion protocols are set forth below as Modified Schedule 1 and Modified Schedule 2.

Administration Details of Modified Schedule 1

In Modified Schedule 1, administration of MM-151 was initiated at a low infusion rate for one hour and the rate was then escalated as described below in the following paragraph. Table III below gives an exemplary dosing schedule for patients getting treatment with a full dose of MM-151 on a weekly basis (QW), every other week (Q2W), or every three weeks (Q3W). Any pretreatment is given before each administration. Herein, this infusion schedule is termed as "Modified Schedule 1."

In Modified Schedule 1, the rates of infusion of MM-151 are carefully controlled to reduce or prevent hypersensitivity reactions (e.g., allergic reactions). Modified Schedule 1 is set forth in Table IV below, and provides a rate escalation schedule for the first two infusions at dose level of 10.5 mg/kg to an 85 kg patient. The infusion rate for Cycle 1 Week 1 begins at 10 mg/hour (1X) for the first 60 minutes followed by an escalation of six subsequent rates for 30 min each—20 mg/hour (2X), 40 mg/hour (4X), 60 mg/hour (6X), 100 mg/hour (10X), 150 mg/hour (15X), and finally 200 mg/hour (20X). The final 200 mg/hour rate is continued until the full dose is delivered (all of these escalation steps occurring over the course of approximately seven hours in total). The infusion rate for Cycle 1 Week 2 and subsequent administrations begins at 50 mg/hour (5X) for the first 60 minutes followed by an escalation of seven subsequent rates for 30 min each—100 mg/hour (10X), 150 mg/hour (15X), 200 mg/hour (20X), 250 mg/hour (25X), 300 mg/hour (30X), 350 mg/hour (35X), and finally 400 mg/hour (40X). The final 200 mg/hour rate is continued until the full dose is delivered (all of these escalation steps occurring over the course of approximately 4.5 hours in total). If a patient experienced an infusion reaction during an infusion, the next full dose was optionally (at the treating physician's discretion) administered with the slower Cycle 1 Week 1 schedule. If a patient did not experience an infusion reaction during an infusion, the next full dose was administered (at the treating physician's discretion) at the faster Cycle 1 Week 2 schedule.

Figure 1B:
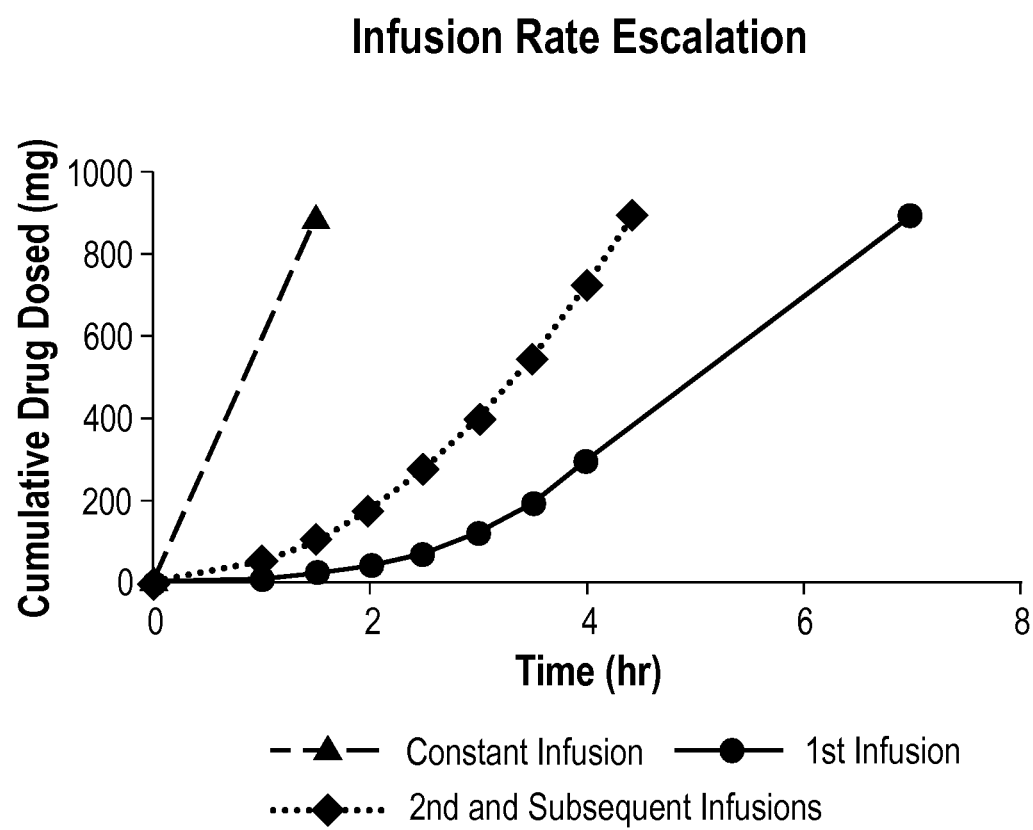
FIG. 1B is a graphic representation of the variations in cumulative drug (mg of MM-151) dosed over time for the data set forth in Table III and Table IV plotted in comparison to constant infusion.

Particular embodiments of this infusion schedule ("Modified Schedule 1") are shown as line plots in FIGS. 1A-1B. FIG. 1A depicts the rate escalation schedules for Cycle 1 Week 1 and the subsequent full dose administration(s) and FIG. 1B shows the cumulative amount of drug administered during these administrations.

TABLE III

Dosage and Administration of MM-151 Monotherapy ("Modified Schedule 1")

| Schedule | Cycle 1 | | | | Subsequent Cycles | | | |
| --- | --- | --- | --- | --- | --- | --- | --- | --- |
| | W1 | W2 | W3 | W4 | W1 | W2 | W3 | W4 |
| QW | FD | FD | FD | FD | FD | FD | FD | FD |
| Q2W | FD | — | FD | — | FD | — | FD | — |
| Q3W | FD | — | — | n/a | FD | — | — | n/a |

TABLE IV

Example of MM-151 administration with an alternative infusion schedule ("Modified Schedule 1") at 10.5 mg/kg for an 85 kg patient

| Infusion | Rate (mg/hour) | Duration (hr) | Drug Infused (mg) | Cumulative Drug Infused (mg) | Cumulative Time (hr) |
|---|---|---|---|---|---|
| 1st Infusion | 10 | 1.0 | 10 | 10 | 1.0 |
| (Cycle 1 | 20 | 0.5 | 10 | 20 | 1.5 |
| Week 1) | 40 | 0.5 | 20 | 40 | 2.0 |
|  | 60 | 0.5 | 30 | 70 | 2.5 |
|  | 100 | 0.5 | 50 | 120 | 2.0 |
|  | 150 | 0.5 | 75 | 195 | 3.5 |
|  | 200 | 3.5 | 697.5 | 892.5 | 7.0 |
| Subsequent | 50 | 1.0 | 50 | 50 | 1.0 |
| Infusions | 100 | 0.5 | 50 | 100 | 1.5 |
| (Cycle 1 | 150 | 0.5 | 75 | 175 | 2.0 |
| Week 2, | 200 | 0.5 | 100 | 275 | 2.5 |
| et seq.) | 250 | 0.5 | 125 | 400 | 3.0 |
|  | 300 | 0.5 | 150 | 550 | 3.5 |
|  | 350 | 0.5 | 175 | 725 | 4.0 |
|  | 400 | 0.4 | 167.5 | 892.5 | 4.42 |

Administration Details of Modified Schedule 2

Three issues arose during the trial in which Modified Schedule 1 was employed. Firstly, the slow infusion schedule required extended administration times (administration of the first full dose of MM-151 extended to two days for almost all patients). Secondly, the large number of rate escalation steps during administration in accordance with Modified Schedule 1 created a significant burden for nursing staff, particularly when infusion reactions occurred, as they required rate de-escalation, resulting in highly complex administration patterns. Thirdly, Modified Schedule 1, while reducing the severity of infusion reactions, did not adequately reduce the frequency with which they occurred—this is believed to have been due to cytokine mediated inflammatory events. Modified Schedule 2 was invented to address these issues.

In Modified Schedule 2, a priming phase designed to enhance the safety and ease of MM-151 administration precedes Cycle 1. The priming phase consists of two weekly fixed doses of 225 mg (Priming Week 1) and 450 mg (Priming Week 2) given prior to Cycle 1. Safety data support the fixed 225 mg and 450 mg doses as they equate to approximately 2.7 mg/kg (2.1 to 3.7, ±S.D) and approximately 5.4 mg/kg (4.2 to 7.4, ±S.D) for the average patient enrolled in this study at the time the clinical trial was modified to include Modified Schedule 2 (84±23kg (mean ±S.D), range 48-169 kg, N=55). Table V below gives an exemplary dosing schedule for patients getting treatment on a weekly basis (QW), every other week (Q2W), or every three weeks (Q3W). Any pretreatment is given before each administration.

In Modified Schedule 2, the rates of infusion of MM-151 are carefully controlled to reduce or prevent both hypersensitivity reactions (e.g., allergic reactions) and cytokine-mediated infusion reactions. Table VI below gives a rate escalation schedule for the first four infusions and includes the Priming Phase and the first two full doses. The infusion rate for Priming Week 1 (W1) begins at 25 mg/hour (1X) for the first 30 minutes, followed by a rate of 50 mg/hour (2X) for the second 30 minutes, and finally followed by 100 mg/hour (4X) until the full dose is delivered at slightly less than three hours. The infusion rate for Priming Week 2 (W2) begins at 1X for the first 30 minutes, followed by a rate of 2X for the second 30 minutes, followed by the rate of 4X for the next 30 minutes, and finally by the rate of 8X until the full dose is delivered at approximately 3 ½ hours. Similarly, the first full dose is administered at the beginning of Cycle 1 beginning with an infusion rate of 50 mg/hour (2X) for the first 30 minutes, and then advanced at the discretion of the treating medical professional, for example, followed by a rate of 4X for the next 30 minutes, followed by a rate of 8X for the next 30 minutes, and finally followed by a rate of 16X until the full dose is administered to the patient. If a patient experiences an infusion reaction on one or both Priming Phase infusions, the first full dose may be administered with a slower schedule beginning with an infusion rate of 50 mg/hour (2X) for the first 30 minutes, and then advanced at the discretion of the treating medical professional, for example, followed by a rate of 4X for the next 30 minutes, followed by a rate of 8X until the full dose is administered to the patient.

Figure 2A:
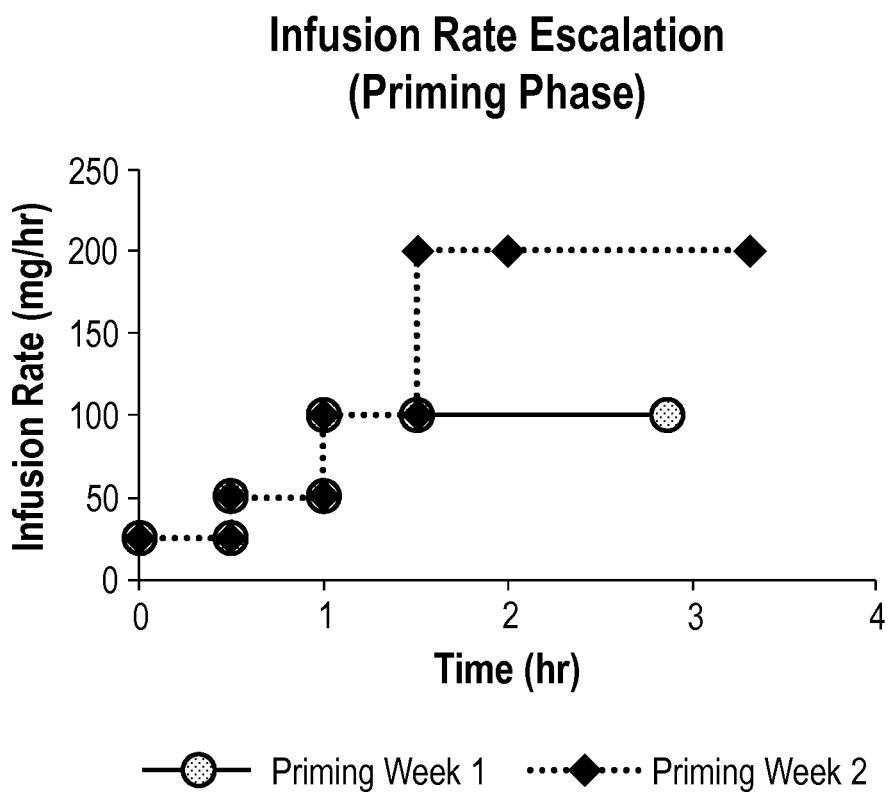
FIG. 2A is a graphic representation of the changes in infusion rate associated with the data set forth in Table V and Table VI for the first infusion ("Priming Week 1") and for the second infusion ("Priming Week 2").
Figure 2B:
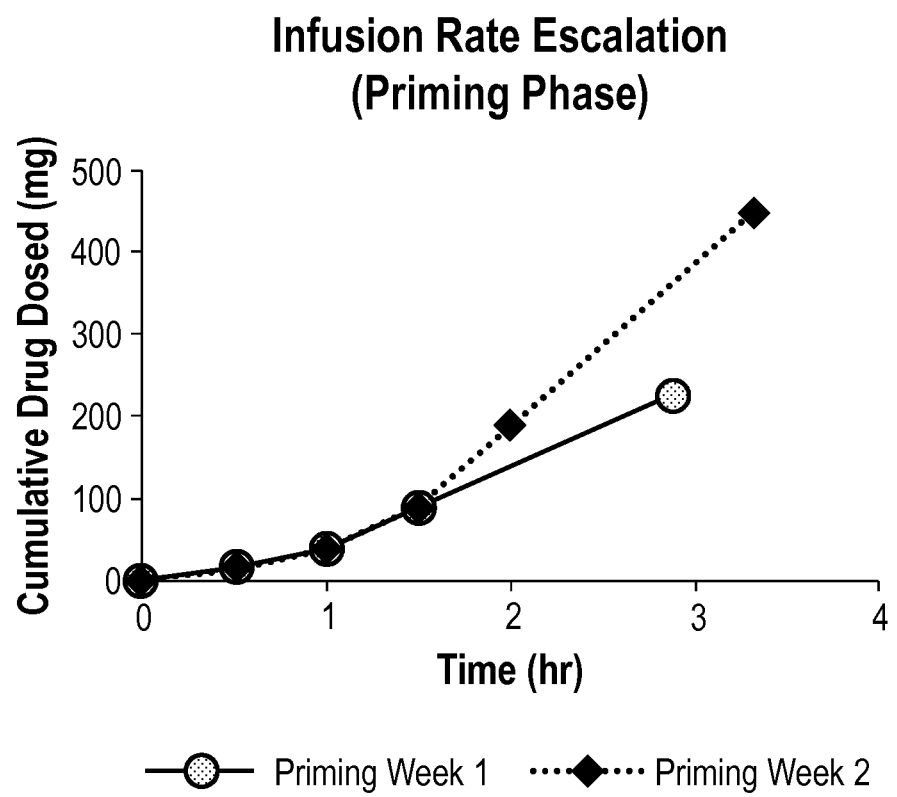
FIG. 2B is a graphic representation of the variations in cumulative drug (mg of MM-151) dosed over time for the data set forth in Table V and Table VI for the first infusion ("Priming Week 1") and for the second infusion ("Priming Week 2").
Figure 2C:
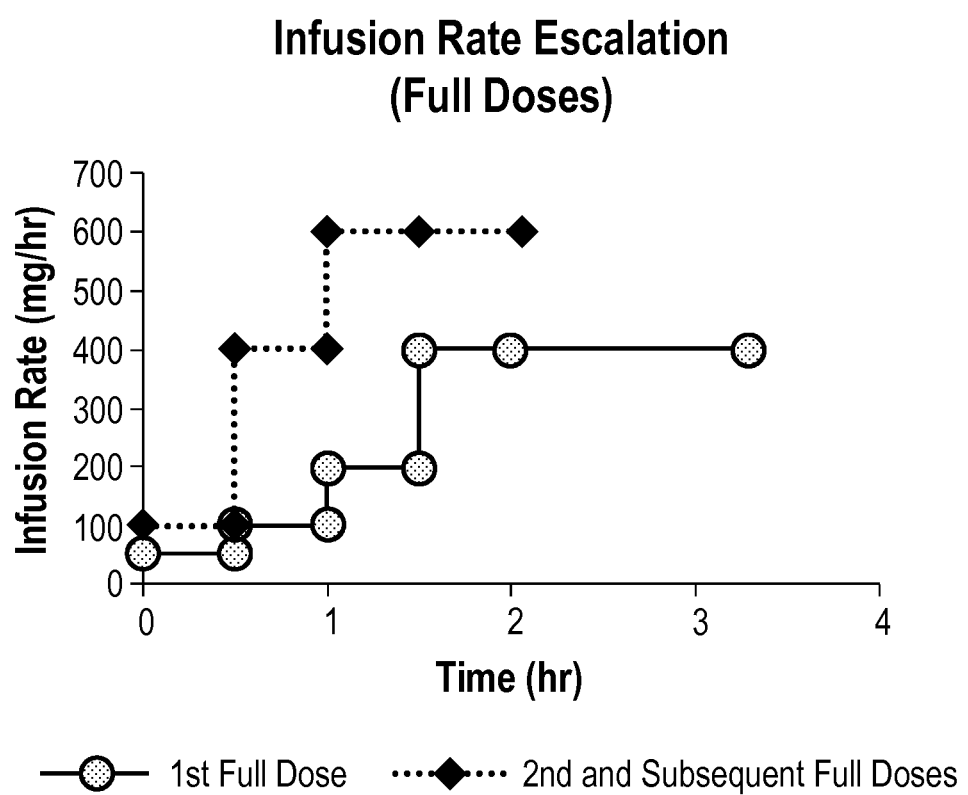
FIG. 2C is a graphic representation of the changes in infusion rate associated with the data set forth in Table V and Table VI for the first full dose and for the second full dose (and subsequent full doses).
Figure 2D:
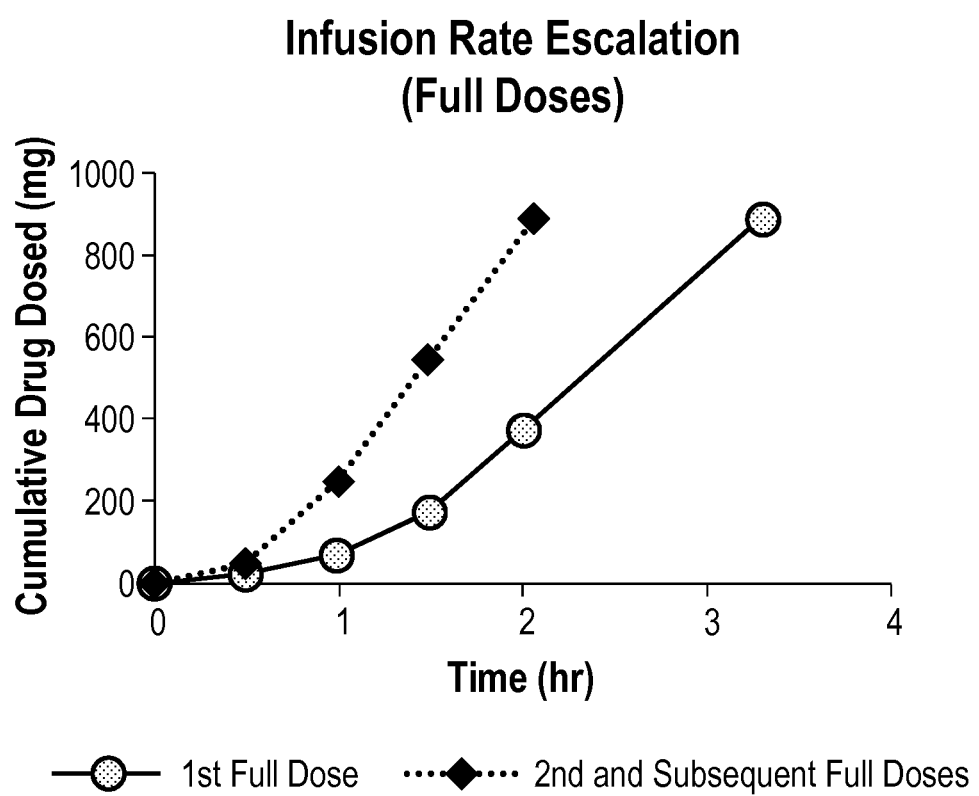
FIG. 2D is a graphic representation of the variations in cumulative drug (mg of MM-151) dosed over time for the data set forth in Table V and Table VI for the first full dose and for the second full dose (and subsequent full doses).

Particular embodiments of this infusion schedule ("Modified Schedule 2") are shown as line plots in FIGS. 2A-2D. FIG. 2A depicts the rate escalation schedules for Priming Week 1 and Priming Week 2. FIG. 2B shows the cumulative amount of drug administered during Priming Week 1 and Priming Week 2. FIG. 2C depicts the rate escalation schedules for Cycle 1 Week 1 and the subsequent full dose administration(s) and FIG. 2D shows the cumulative amount of drug administered during these administrations.

TABLE V

Dosage and Administration of MM-151 Monotherapy ("Modified Schedule 2")

| Schedule | Priming Phase[1] | | Cycle 1 | | | | Subsequent Cycles | | | |
|---|---|---|---|---|---|---|---|---|---|---|
|  | W1 | W2 | W1 | W2 | W3 | W4 | W1 | W2 | W3 | W4 |
| QW | 225 mg | 450 mg | FD | FD | FD | FD | FD | FD | FD | FD |
| Q2W | 225 mg | 450 mg | FD | — | FD | — | FD | — | FD | — |
| Q3W | 225 mg | 450 mg | FD | — | — | n/a | FD | — | — | n/a |

[1]DLT evaluation period will consist of both the Priming Phase and cycle 1

TABLE VI

MM-151 administration with the optimized infusion schedule ("Modified Schedule 2") at 10.5 mg/kg for an 85 kg patient

| Infusion | Rate (mg/hour) | Time (hr) | Drug Infused (mg) | Cumulative Drug Infused (mg) | Cumulative Time (hr) |
|---|---|---|---|---|---|
| 1st Infusion | 25 | 0.5 | 12.5 | 12.5 | 0.5 |
| (Priming Week 1) | 50 | 0.5 | 25.0 | 37.5 | 1.0 |
|  | 100 | 1.875 | 187.5 | 225.0 | 2.88 |
| 2nd Infusion | 25 | 0.5 | 12.5 | 12.5 | 0.5 |
| (Priming Week 2) | 50 | 0.5 | 25.0 | 37.5 | 1.0 |
|  | 100 | 0.5 | 50.0 | 87.5 | 1.5 |
|  | 200 | 1.81 | 362.5 | 450 | 3.31 |

TABLE VI-continued

MM-151 administration with the optimized infusion schedule ("Modified Schedule 2") at 10.5 mg/kg for an 85 kg patient

| Infusion | Rate (mg/hour) | Time (hr) | Drug Infused (mg) | Cumulative Drug Infused (mg) | Cumulative Time (hr) |
|---|---|---|---|---|---|
| 3$^{rd}$ Infusion | 50 | 0.5 | 25 | 25 | 0.5 |
| (1$^{st}$ Full Dose[1]) | 100 | 0.5 | 50 | 75 | 1.0 |
|  | 200 | 0.5 | 100 | 175 | 1.5 |
|  | 400 | 1.794 | 717.5 | 892.5 | 3.29 |
| 4$^{th}$ Infusion | 100 | 0.5 | 50 | 50 | 0.5 |
| (2$^{nd}$ Full Dose[1]) | 400 | 0.5 | 200 | 250 | 1.0 |
|  | 600 | 1.07 | 642.5 | 892.5 | 2.07 |

[1]For this embodiment, a Full Dose is 10.5 mg/kg (892.5 mg for an 85 kg patient)

Results of Administration of MM-151 by Constant Infusion, "Modified Schedule 1" and "Modified Schedule 2"

Figure 3:
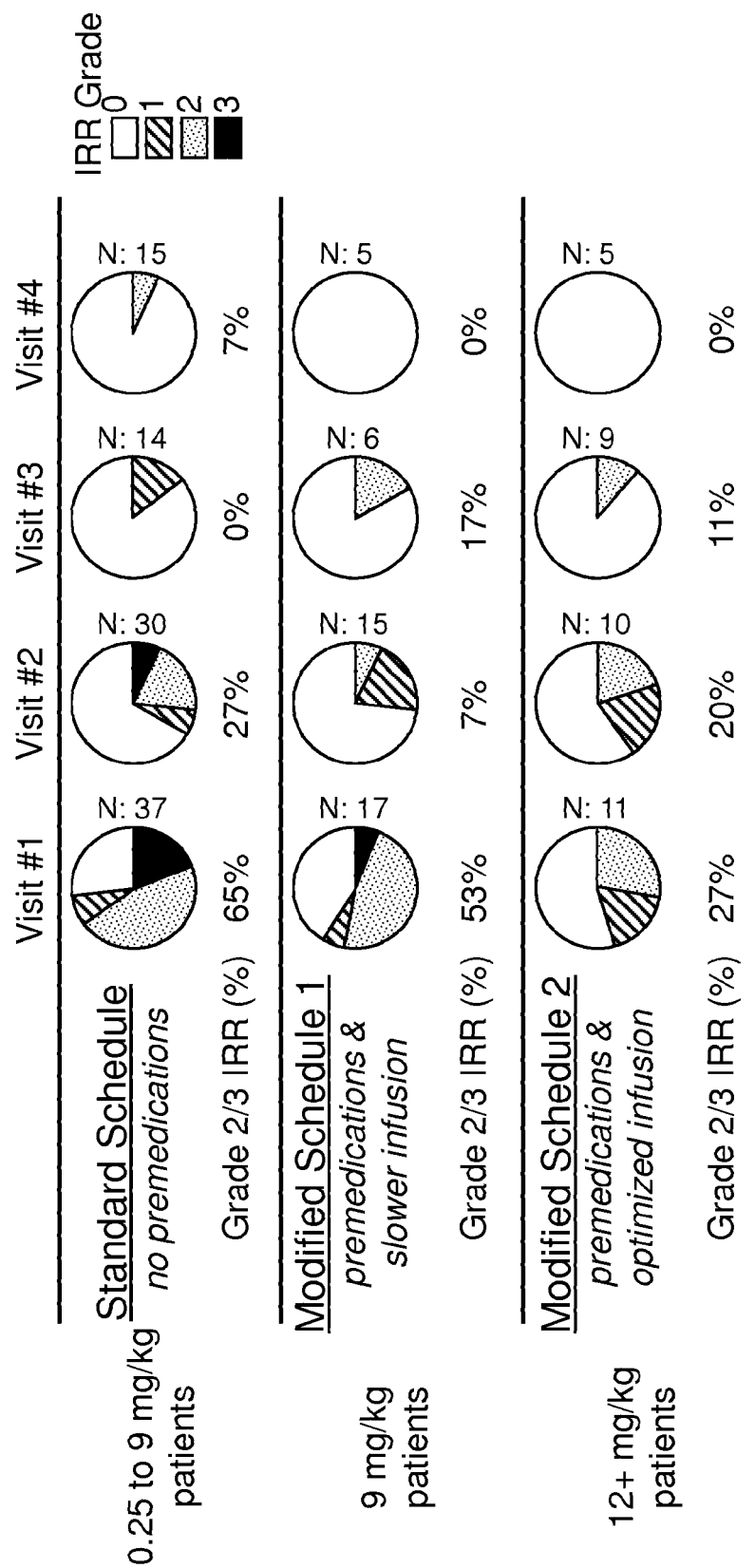
FIG. 3 summarizes data from patients that received MM-151 according to the following regimens: Top row of pie charts: 0.25 to 9 mg/kg MM-151 infusion on a standard schedule (no rate optimization or premedication, top line). Middle row of pie charts: 9 mg/kg MM-151 on Modified Schedule 1 (slower than usual infusion, middle line). Bottom row of pie charts: data patients treated with MM-151 monotherapy comprising two priming doses, one of 225 mg and one of 450 mg, followed by two full doses (as opposed to priming doses) of ≥10.5mg/kg on Modified Schedule 2 (with premedication, bottom line).

Results are shown as pie charts in FIG. 3 for patients who were administered MM-151 by three infusion schedules—constant infusion over 60 to 90 min ("Standard Schedule"), Modified Schedule 1, or Modified Schedule 2. As shown in the figure, patients receiving MM-151 via Modified Schedule 1 (middle row) had fewer Grade 3 infusion reactions, but a similar frequency of Grade 2 infusion reactions at the first visit, and no infusion reactions at all by the time of the fourth visit, even though these patients received a greater dose of drug (up to 9 mg/kg for some patients) than the patients on the Standard Schedule. As also shown in the figure, patients receiving MM-151 via Modified Schedule 2 (bottom row) had no Grade 3 infusion reactions, had fewer Grade 2 infusion reactions than patients in the other groups at the first visit, and no infusion reaction at all by the time of the fourth visit, even though these patients received a greater dose of drug (up to 15 mg/kg for some patients) in the third and fourth administrations than patients in the other groups. In FIG. 3, patients who missed a visit but continued therapy were recorded as missing for the pie chart corresponding to the missed visit.

Figure 4:
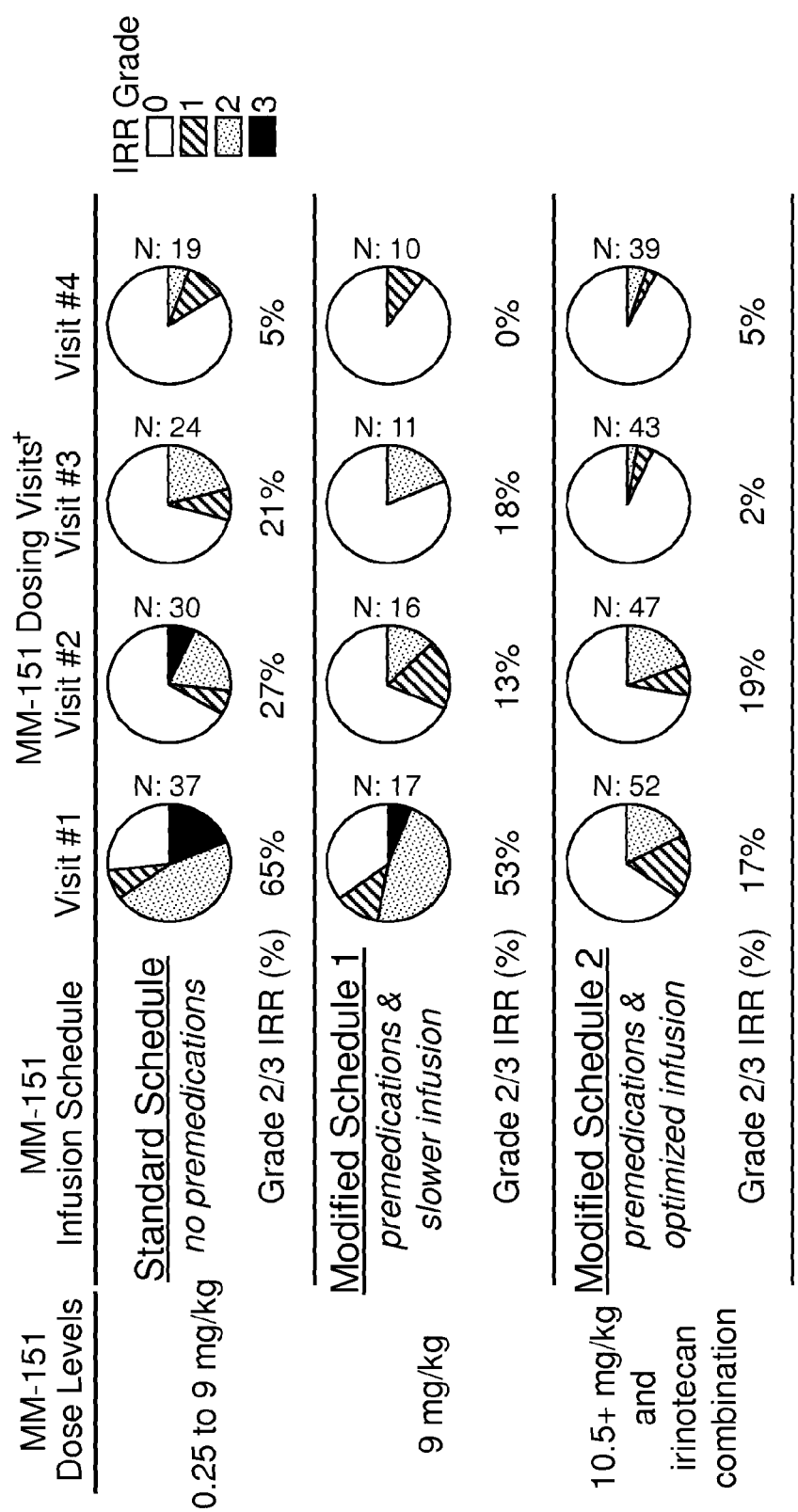
FIG. 4 summarizes data from patients that received MM-151 following the generation of the data presented in FIG. 3, including 65 patients included in FIGS. 3 and 41 additional patients administered MM-151 according to Modified Schedule 2 in the clinical trial. Some of these 41 additional patients were administered MM-151 in combination with irinotecan with a MM-151 dose of 4.5, 6, 7.5, or 9 mg/kg (these data were combined because no effect was seen of irinotecan co-administration on the frequency or severity of IRRs).

Additional results are shown as pie charts in FIG. 4 and include 41 additional patients administered MM-151 according to Modified Schedule 2 in the clinical trial following the generation of the data presented in FIG. 3, including patients administered MM-151 in combination with irinotecan. As shown in the figure, patients receiving MM-151 via the optimized infusion schedule (bottom line) had no Grade 3 infusion reactions and had fewer Grade 2 infusion reactions than patients in the other groups, even though these patients received a greater dose of drug (up to 20 mg/kg for some patients) in the third and fourth administrations than patients in the other groups. In FIG. 4, patients who missed a visit but continued therapy were recorded as present for the next numbered visit, so that the data shown are for the first four administrations, regardless of gaps between visits.

Example 3

Dosage and Administration of MM-151+Irinotecan Combination Therapy (with MM-151 Administered According to "Modified Schedule 2" at Weekly or Biweekly Dosing Intervals)

TABLE VIIa

Dosage of MM-151 + Irinotecan

| | Priming Phase[1] | | Cycle 1 | | | | Subsequent Cycles | | | |
|---|---|---|---|---|---|---|---|---|---|---|
| | W1 | W2 | W1 | W2 | W3 | W4 | W1 | W2 | W3 | W4 |
| MM-151 | 225 mg | 450 mg | FD | FD | FD | FD | FD | FD | FD | FD |
| Irinotecan | 180 | — | 180 | — | 180 | — | 180 | — | 180 | — |

[1]DLT evaluation period will consist of both the Priming Phase and cycle 1

TABLE VIIb

MM-151 + Irinotecan Combination Dose Escalation - Q2W dosing, 2 week Priming Phase, Fixed Dosing

| | Priming Phase[1] | | Cycle 1 | | | | Subsequent Cycles | | | |
|---|---|---|---|---|---|---|---|---|---|---|
| | W1 | W2 | W1 | W2 | W3 | W4 | W1 | W2 | W3 | W4 |
| MM-151 | 225 mg | 450 mg | FD | — | FD | — | FD | — | FD | — |
| Irinotecan | 180 | — | 180 | — | 180 | — | 180 | — | 180 | — |

[1]DLT Evaluation Period = Priming phase + Cycle 1

Example 4

Alternative Dosing Schedule for MM-151

The following tables highlight alternative MM-151 monotherapy and MM-151+irinotecan infusion schemas. The schedule set forth in Table VIII is less preferred because it requires multiple days for initial infusions of MM-151.

TABLE VIII

MM-151 Monotherapy Dose Escalation - 2 Day First Infusion

| | Cycle n | | | |
|---|---|---|---|---|
| Schedule | W 1 | W 2 | W 3 | W 4 |
| QW | D0 - 25-50%[1] D 1 - 50-75% | FD | FD | FD |
| Q2 W | D 0 - 25-50% D 1 - 50-75% | — | FD | — |

[1]D 0 = Day 0 - administer 25-50% of current MM-151 mg/kg dose level;
D 1 = Day 1 - administer remaining MM-151 at 50-75% of current dose level; MM-151 administration over 2 subsequent days occurs only for the first MM-151 dose in cycle 1

Example 5

Alternative dosing schedules for MM-151 "Modified Schedule 3"

Modified Schedule 3 uses the rate escalation scheme set forth in Modified Schedule 2 with dosing set in terms of mg/kg (body weight based dosing) rather than mg/patient (fixed dose per patient). The 225 mg fixed dose of Modified Schedule 2 is replaced with a 3 mg/kg dose in Modified Schedule 3, and the 450 mg fixed dose of Modified Schedule 2 is replaced with a 6 mg/kg dose in Modified Schedule 3. Following the 2-week priming phase, full doses (FD) of MM-151 are administered QW, Q2W, or Q3W as indicated.

TABLE IX

MM-151 Monotherapy Dose Escalation - 2 week Priming Phase, mg/kg Dosing

| Schedule | Priming Phase[1] | | Cycle 1 | | | | Subsequent Cycles | | | |
|---|---|---|---|---|---|---|---|---|---|---|
| | W1 | W2 | W1 | W2 | W3 | W4 | W1 | W2 | W3 | W4 |
| QW | 3 | 6 | FD | FD | FD | FD | FD | FD | FD | FD |
| Q2W | 3 | 6 | FD | — | FD | — | FD | — | FD | — |
| Q3W | 3 | 6 | FD | — | — | — | FD | — | — | — |

[1]Priming phase only precedes cycle 1; Subsequent cycles have no priming phase; DLT Evaluation Period = Priming phase + Cycle 1

TABLE X

MM-151 + Irinotecan Combination Dose Escalation - 2 week Priming Phase, mg/kg Dosing

| | Priming Phase[1] | | Cycle 1 | | | | Subsequent Cycles | | | |
|---|---|---|---|---|---|---|---|---|---|---|
| | W1 | W2 | W1 | W2 | W3 | W4 | W1 | W2 | W3 | W4 |
| MM-151 | 3 | 6 | FD | FD | FD | FD | FD | FD | FD | FD |
| Irinotecan | 180 | — | 180 | — | 180 | — | 180 | — | 180 | — |

[1]DLT Evaluation Period = Priming phase + Cycle 1

TABLE XI

MM-151 + Irinotecan Combination Dose Escalation - Q2W dosing, 2 week Priming Phase, mg/kg Dosing

| | Priming Phase[1] | | Cycle 1 | | | | Subsequent Cycles | | | |
|---|---|---|---|---|---|---|---|---|---|---|
| | W1 | W2 | W1 | W2 | W3 | W4 | W1 | W2 | W3 | W4 |
| MM-151 | 3 | 6 | FD | — | FD | — | FD | — | FD | — |
| Irinotecan | 180 | — | 180 | — | 180 | — | 180 | — | 180 | — |

[1]DLT Evaluation Period = Priming phase + Cycle 1

Example 6

Adjustment of Administration of MM-151 if an Infusion-Related Reaction Occurs

The following schema highlights the management of infusion reactions that may occur during the administration of MM-151. This schema incorporates the grading of infusion-related reactions as defined by the National Cancer Institute Common Terminology Criteria for Adverse Events (Version 4.0; as described in the Background above).

If a patient experiences a Grade 1 infusion-related reaction (lowest severity), the infusion may proceed according to the infusion schedule and the symptoms should be monitored by the treating physician (or nurse or other medical staff). At the discretion of the treating physician, additional medication may be administered, preferably one or both of a histamine H1 blocker and an anti-inflammatory steroid.

If a patient experiences a Grade 2 infusion-related reaction (moderate severity), the infusion of MM-151 should be interrupted and additional medication administered, preferably one or both of a histamine H1 blocker and an anti-inflammatory steroid. If the infusion-related reaction symptoms resolve during the interruption, the infusion may be resumed at a rate equal to or lower than the rate at the time of the interruption. In one embodiment, the infusion may resume at a rate that is approximately (or exactly) 50% of the rate at the time of the interruption. In another embodiment, the infusion rate is initially lowered and is subsequently escalated, optionally until it reaches or exceeds the rate at the time of the interruption. Preferably, the remaining steps set forth in the infusion rate schedule for the dosing visit will be carried out to effect the rate escalation.

If a patient experiences a Grade 3 or a Grade 4 infusion-related reaction (severe), the infusion of MM-151 should be terminated and additional medication administered, preferably one or both of a histamine H1 blocker and an anti-inflammatory steroid. Additional medication such as one or both of a bronchodilator and epinephrine should be administered. The patient should be monitored by the treating physician for worsening of symptoms and treated accordingly. If a patient experiences a Grade 3 infusion-related reaction, the administration of MM-151 may resume at the next scheduled dosing visit at the discretion of the treating physician. If a patient experiences a Grade 4 infusion-related reaction, MM-151 should not be administered to the patient at any subsequent visit.

An exemplary embodiment of this schema is set forth below and highlights the activities that the treating physician may undertake if a patient exhibits an infusion-related reaction. These guidelines may be altered at the discretion of the treating physician and/or by the guidelines in place at the medical institution where the administration of MM-151 is being performed.

If a patient exhibits a Grade 1 infusion-related reaction:
  Maintain the infusion rate unless progression of symptoms to ≥Grade 2; if symptoms worsen, refer to the guidelines below.
  Consider treating the patient with additional medication with diphenhydramine 25-50 mg p.o. or i.v. and/or methylprednisolone 125 mg (or equivalent) i.v.
  Monitor the patient every 15 minutes for worsening of condition.

If a patient exhibits a Grade 2 infusion-related reaction:
  Interrupt the infusion and, at the discretion of the treating clinician, disconnect the infusion tubing from the patient.
  Administer additional medication with diphenhydramine 25-50 mg p.o. or i.v. and/or methylprednisolone 125 mg (or equivalent) i.v.
  Monitor the patient every 15 minutes for worsening of condition (preferably until symptoms resolve).
  After recovery from symptoms, resume the infusion rate at 50% of the previous rate and if no further symptoms appear, increase rate stepwise until the infusion is completed.
  If Grade 2 symptoms recur, disconnect the infusion tubing from patient and do not restart the infusion.

If all symptoms have resolved after 7 days, the patient may be administered MM-151 at the next scheduled dosing visit.

If symptoms worsen to ≥Grade 3 at any time, follow the guidelines below.

If a patient exhibits a Grade 3 infusion-related reaction:

Interrupt the infusion and disconnect the infusion tubing from the patient.

Administer diphenhydramine 25-50 mg i.v.

Administer 1) normal saline 2) epinephrine (0.2-0.5 mL of a 1:1000 dilution (0.2-0.5 mg) subcutaneous (s.q.) or intramuscular (i.m.) and 3) bronchodilators (nebulized albuterol 2.5-5 mg in 3 mL of saline), as medically indicated.

Consider additional medication with methylprednisolone 125 mg (or equivalent) i.v.

Monitor the patient every 15 minutes for worsening of condition (preferably until symptoms resolve).

If the symptoms improve and the patient is discharged, advise patient to seek emergency treatment and notify the treating clinician if the infusion reaction symptoms recur after discharge from the clinic.

Depending on the severity and persistence of the reaction, the treating physician may consider administration of MM-151 at the next scheduled dosing visit.

If a patient exhibits a Grade 4 infusion-related reaction:

Interrupt the infusion and disconnect the infusion tubing from the patient.

Administer diphenhydramine 50 mg i.v.

Administer 1) normal saline 2) epinephrine (0.2-0.5 mL of a 1:1000 dilution (0.2-0.5 mg) s.q. or i.m. and 3) bronchodilators (nebulized albuterol 2.5-5 mg in 3 mL of saline), as medically indicated.

Consider additional medication with methylprednisolone (or equivalent) i.v. up to 0.5 mg/kg Q 6 h) to prevent recurrent or ongoing reactions.

Monitor the patient every 15 minutes for worsening of condition (preferably until symptoms resolve).

Consider hospital admission for observation.

Do not re-administer MM-151 to the patient.

Equivalents

Those skilled in the art will recognize, or be able to ascertain using no more than routine experimentation, many equivalents of the specific embodiments described herein. Such equivalents are intended to be encompassed by the following claims. Any combination of the embodiments disclosed in the any plurality of the dependent claims or Examples is contemplated to be within the scope of the disclosure.

Incorporation by Reference

The disclosure of each and every U.S. and foreign patent and pending patent application and publication referred to herein is specifically incorporated herein by reference in its entirety, as are the contents of Sequence Listing and Figures.

What is claimed is:

1. A method of administering a mixture of three monoclonal IgG1 anti-EGFR antibodies to a human cancer patient, the method comprising initially administering the mixture to the patient as a first and a second intravenous infusion over a two week cycle as priming doses in sequence as set forth in the following table:

| Infusion | Infusion Rate Sequence[1] | Infusion Rate (mg/hr) | Mixture Infused (mg) | Cumulative Mixture Infused (mg) |
|---|---|---|---|---|
| 1st Infusion (Priming Week 1) | 1st Rate | 25 | 12.5 | 12.5 |
| | 2nd Rate | 50 | 25.0 | 37.5 |
| | 3rd Rate | 100 | 187.5 | 225.0 |
| 2nd Infusion (Priming Week 2) | 1st Rate | 25 | 12.5 | 12.5 |
| | 2nd Rate | 50 | 25.0 | 37.5 |
| | 3rd Rate | 100 | 50.0 | 87.5 |
| | 4th Rate | 200 | 362.5 | 450 |

[1]per infusion wherein the 1st infusion of the mixture is administered during the priming week 1 at the 1st rate for a ½ hour, immediately followed by the 2nd rate for a second ½ hour, immediately followed by the 3rd rate until all of the first dose and 225 mg of mixture has been administered;

wherein the 2nd infusion of the mixture is administered during priming week 2 at the 1st rate for a ½ hour, immediately followed by the 2nd rate for the second ½ hour, immediately followed by the 3rd rate for a ½ hour, immediately followed by the 4th rate until all of the first dose and 450 mg of mixture has been administered;

wherein, prior to each infusion of the mixture of anti-EGFR antibodies, diphenhydramine is administered to the patient orally or intravenously at a dose of 25 mg-50 mg and methylprednisolone is administered to the patient intravenously at a dose of 25-125 mg; and wherein the mixture comprises:

i) a first monoclonal antibody comprising heavy chain CDRs 1, 2 and 3 set forth in SEQ ID NOs: 7, 8 and 9 respectively, and light chain CDRs 1, 2 and 3 set forth in SEQ ID NOs: 10, 11 and 12 respectively;

ii) a second monoclonal antibody comprising heavy chain CDRs 1, 2 and 3 set forth in SEQ ID NOs: 13, 14 and 15 respectively and light chain CDRs 1, 2 and 3 set forth in SEQ ID NOs: 16, 17, and 18 respectively; and iii) a third monoclonal antibody comprising heavy chain CDRs 1, 2 and 3 set forth in SEQ ID NOs: 19, 20 and 21 respectively, and light chain CDRs 1, 2 and 3 set forth in SEQ ID NOs: 22, 23 and 24 respectively;

wherein the first antibody, the second antibody, and the third antibody are formulated in a mixture at a molar ratio to each other of 2:2:1, respectively;

wherein the mixture of three monoclonal IgG1 anti-EGFR antibodies is administered to a human cancer patient diagnosed with colorectal cancer, in combination with liposomal irinotecan.

2. The method of claim 1, wherein the dose of methylprednisolone is 125 mg.

3. The method of claim 1, wherein the first antibody comprises a heavy chain variable region comprising SEQ ID NO:1 and a light chain variable region comprising SEQ ID NO:2, the second antibody comprises a heavy chain variable region comprising SEQ ID NO:3 and a light chain variable region comprising SEQ ID NO:4; and the third antibody comprises a heavy chain variable region comprising SEQ ID NO:5 and a light chain variable region comprising SEQ ID NO:6.

4. The method of claim 1, wherein, prior to each infusion of the mixture of anti-EGFR antibodies, acetaminophen is administered to the patient at a dose of 650 mg.

5. The method of claim 1, wherein the mixture of three monoclonal IgG1 anti-EGFR antibodies is MM-151.

6. The method of claim 1, wherein the mixture of three monoclonal IgG1 anti-EGFR antibodies is administered in further combination with 5-fluorouracil and leucovorin.

\* \* \* \* \*